US010842767B2

(12) United States Patent
D'Agostino et al.

(10) Patent No.: US 10,842,767 B2
(45) Date of Patent: *Nov. 24, 2020

(54) USE OF KETONE ESTERS FOR PREVENTION OF CNS OXYGEN TOXICITY

(71) Applicant: University of South Florida, Tampa, FL (US)

(72) Inventors: Dominic Paul D'Agostino, Tampa, FL (US); Jay B. Dean, Land O'Lakes, FL (US); Raffaele Pilla, Tampa, FL (US); Patrick Arnold, Champaign, IL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/078,066

(22) Filed: Nov. 12, 2013

(65) Prior Publication Data

US 2014/0073693 A1 Mar. 13, 2014

Related U.S. Application Data

(63) Continuation of application No. PCT/US2012/037099, filed on May 9, 2012.

(60) Provisional application No. 61/483,927, filed on May 9, 2011, provisional application No. 61/579,779, filed on Dec. 23, 2011.

(51) Int. Cl.
*A61K 31/225* (2006.01)
*A61K 31/22* (2006.01)

(52) U.S. Cl.
CPC ............ *A61K 31/225* (2013.01); *A61K 31/22* (2013.01)

(58) Field of Classification Search
CPC ... A61K 31/22; A61K 31/225; A61K 2300/00
See application file for complete search history.

(56) References Cited

PUBLICATIONS

Chavko et al. (Nitric Oxide vol. 9, Issue 1, Aug. 2003, pp. 18-23).*
Puchowicz et al. (Journal Nutrition Biochemistry 11: 281-287, 2000).*
N. Bitterman, et al., The Effect of Sodium Phenytoin on Central Nervous System Oxygen Toxicity. Aviation, Space, and Environmental Medicine, Mar. 1987, pp. 224-226.
N. Bitterman, et al., Starvation and Dehydration attenuate CNS Oxygen Toxicity in Rats. Brain Research, vol. 761, (1997), pp. 146-150.
K. Bough, et al., Anticonvulsant Mechanisms of the Ketogenic Diet. Epilepsia, vol. 48, No. 1, (2007), pp. 43-58.
George F. Cahill, Jr., Fuel Metabolism in Starvation, Annu. Rev. Nutr. (2006) vol. 26, pp. 1-22.
M. Chavko, et al., Effect of MK-801 on Seizures Induced by Exposure to Hyperbaric Oxygen: Comparison with AP-7. Toxicology and Applied Pharmacology, vol. 151, (1998), pp. 222-228.
M. Chavko, et al., Attenuation of Brain Hyperbaric Oxygen Toxicity of Fasting is Not Related to Ketosis. Undersea and Hyperbaric Medical Society, Inc., (1999), pp. 99-103.
S. Ciraolo, et al., Model of Extreme Hypoglycemia in Dogs Made Ketotic with (R,S)-1,3-butanediol Acetoacetate Esters. American Journal of Physiology—Endocrinology and Metabolism, vol. 269, (1995), pp. E67-E75.
Dominic P. D'Agostino, et al., Superoxide (O2-) Production in CA1 Neurons of Rat Hippocampal Slices Exposed to Graded Levels of Oxygen. J. Neurophysiol, vol. 98, (2007), pp. 1030-1041.
I. Demchenko, et al., Oxygen Seizure Latency and Peroxynitrite formation in Mice Lacking Neuronal or Endothelial Nitric Oxide Synthases. Neuroscience Letters, vol. 344 (2003) pp. 53-56.
S. Desrochers, et al., Metabolism of (R,S)-1,3-butanediol acetoacetate esters, potential parenteral, and enteral nutrients in conscious pigs. 1,3-Butanediol Acetoacetate Metabolism, (1995), pp. E660-E667.
J. Freeman, et al., Ketosis and the Ketogenic Diet, 2010: Advances in Treating Epilepsy and Other Disorders. Advances in Pediatrics, vol. 57, (2010), pp. 315-329.
M. Gasior, et al., The Anticonvulsant Activity of Acetone, the Major Ketone Body in the Ketogenic Diet, Is Not Dependent on Its Metabolites Acetol, 1,2-Propanediol, Methylglyoxal, or Pyruvic acid. Epilepsia, vol. 48, Issue 4, (2007), pp. 793-800.
R. Gerschman, et al., Oxygen Poisoning and X-irradiation: A Mechanism in Common. Science, vol. 119, May 7, 1954, pp. 623-626.
A. Greene, et al., Perspectives on the Metabolic Management of Epilepsy through Dietary Reduction of Glucose and Elevation of Ketone Bodies. Journal of Neurochemistry, 2003, vol. 86, pp. 529-537.
M. Habib, et al., Ethane Production Rate in Vivo is Reduced with Dietary Restriction. Journal of Applied Physiology, vol. 68, 1990, pp. 2588-2590.
S. Henderson, et al., Ketone Bodies as a Therapeutic for Alzheimer's Disease. Neurotherapeutics: The Journal of the American Society for Experimental NeuroTherapeutics, vol. 5, (2008), pp. 470-480.
International Search Report and Written Opinion for International Application No. PCT/US2012/037099, filing date of May 9, 2012, dated Jan. 2, 2013.

(Continued)

*Primary Examiner* — Kortney L. Klinkel
*Assistant Examiner* — William Y Lee
(74) *Attorney, Agent, or Firm* — Meunier Carlin & Curfman LLC

(57) ABSTRACT

The present invention demonstrates the therapeutic use of ketone esters for seizure disorders, Alzheimer's disease and malignant brain cancer, which are associated with metabolic dysregulation. The administration of ketone esters resulted therapeutic ketosis and neuroprotection against seizures resulting from CNS oxygen toxicity. Supplemental ketones were also found to reduce superoxide production in cultured cortex neurons exposed to hyperbaric oxygen and Aβ-42, and to decrease proliferation and viability in U87 glioma cells. These observations support the therapeutic effect of ketones for seizure disorders, Alzheimer's disease and malignant brain cancer. The ketone esters may be derived from acetoacetate and can include R,S-1,3-butanediol acetoacetate monoester, R,S-1,3-butanediol acetoacetate diester, or a combination of the two.

11 Claims, 31 Drawing Sheets

(56) References Cited

PUBLICATIONS

N. Juge, et al., Metabolic Control of Vesicular Glutamate Transport and Release. Neuron, vol. 68, 2010, pp. 99-112.

D.Y. Kim, et al., Ketones prevent synaptic dysfunction induced by mitochondrial respiratory complex inhibitors. Journal of Neurochemistry, vol. 114, 2010, pp. 130-141.

P. Klein, et al., Ketogenic diet treatment in adults with refractory epilepsy. Epilepsy & Behavior, vol. 19, 2010, pp. 575-579.

S. Likhodii, et al., Acetone as an Anticonvulsant. Epilepsia, vol. 49, (Suppl. 8), 2008, pp. 83-86.

S. Likhodii, et al., Anticonvulsant Properties of Acetone, A Brain Ketone Elevated by the Ketogenic Diet. Annals of Neurology, vol. 54, No. 2, Aug. 2003, pp. 219-226.

M. Maalouf, et al., Ketones Inhibit Mitochondrial Production of Reactive Oxygen Species Production Following Glutamate Excitotoxicity by Increasing NADH Oxidation. Neuroscience, vol. 145, (2007), pp. 256-264.

M. Maalouf, et al., The Neuroprotective properties of calorie restriction, the ketogenic diet, and ketone bodies. Brain Research Reviews, vol. 59, (2009), pp. 293-315.

M. McNally, et al., Ketone Bodies in Epilepsy, Journal of Neurochemistry, vol. 121, (2012), pp. 28-35.

J. Milder, et al., Acute Oxidative Stress and Systemic Nrf2 Activation by the Ketogenic diet. Neurobiology of Disease, vol. 40 (2010) pp. 238-244.

J. Rho, et al., Acetoacetate, Acetone, and Dibenzylamine (a Contaminant in L-(+)-B-Hydroxybutyrate) Exhibit Direct Anticonvulsant Actions in Vivo. Epilepsia, vol. 43, Issue 4, (2002), pp. 358-361.

J. Rho, et al., The Ketogenic diet in a pill: Is this possible? Epilepsia, vol. 49 (suppl. 8), 2008, pp. 127-133.

R. Veech, The Therapeutic implications of Ketone Bodies: The Effects of Ketone Bodies in Pathological Conditions: Ketosis, Ketogenic diet, redox states, insulin resistance, and mitochondrial metabolism. Prostaglandins, Leukotrienes and Essential Fatty Acids, vol. 70, (2004), pp. 309-319.

G. Yellen, Ketone Bodies, Glycolysis, and KATP Channels in the Mechanism of the Ketogenic diet. Epilepsia, vol. 49 (Suppl. 8), 2008, pp. 80-82.

D'Agostino, et al., Therapeutic ketosis with ketone ester delays central nervous system oxygen toxicity in rats. Am J Physiol Regul Integr Comp Physiol. May 15, 2013;304(10):R829-36.

Bitterman & Ben-Amotz, Beta-carotene and CNS oxygen toxicity in rats. J Appl Physiol. Mar. 1994;76(3):1073-6.

Chavko, et al., Attenuation of brain hyperbaric oxygen toxicity by fasting is not related to ketosis. Undersea Flyperbar Med. 1999 Summer;26(2);99-103.

D'Agostino, et al., Superoxide (*O2-) production in CA1 neurons of rat hippocampal slices exposed to graded levels of oxygen. J Neurophysiol. Jun. 6, 2007;98(2)1030-41.

Lin & Jamieson, Effects of antioxidants on oxygen toxicity in vivo and lipid peroxidation in vitro. Pharmacol Toxicol. Apr. 1992;70(4):271-7.

Kossoff, Eric H. et al. The Ketogenic and Modified Atkins Diets, 2016, pp. 12-13. Printed in the United States of America by McNaughton & Gunn.

D'Agostino, Dominic P. et al. Therapeutic ketosis with ketone ester delays central nervous system oxygen toxicity seisures in rats. Am J Physiol Regul Integr Comp Physiol 304: R829-R836, 2013. First published Apr. 3, 2013; doi:10.1152/ajpregu.00506.2012.

Garcia III, Alfredo J. et al. Hyperbaric hyperoxia and normobaric reoxygenation increase excitability and activate oxygen-induced potentiation in CA1 hippocampal neurons. J Appl Physiol 109: 804-819, 2010. First published Jun. 17, 2010; doi:10.1152/japplphysiol.91429.2008.

Kesl, Shannon L. et al. Effects of exogenous ketone supplementation on blood ketone, glucose, triglyceride, and lipoprotein levels in Sprague-Dawley rats. Nutrition & Metabolism (2016) 13:9.

McDonald, Lyle. The Ketogenic Diet. A Complete Guide for the Dieter and Practitioner, 1998, Chapter 1.

Liberti, Maria V. and Jason W. Locasale. The Warburg Effect: How Does it Benefit Cancer Cells? Trends in Biochemical Sciences, Mar. 2016. vol. 41, No. 3, pp. 211-218.

Lo, Eng H. et al. Mechanisms, Challenges and Opportunities in Stroke. Nature Reviews, NeuroScience, May 2003. vol. 4, pp. 399-415.

Test ID: BYHD. Beta-Hydroxybutyrate, Serum. Mayo Clinic. Mayo Medical Laboratories.

Brian, Johnny E. Current Thoughts on Mechanisms of Hyperoxic Seizures. http://www.johnchatterton.com/wp-content/uploads/2013/03/MechanismsofHyperoxicSeizures.pdf, last accessed Jun. 12, 2017.

Kim, Do Young et al. Ketones prevent synaptic dysfunction induced by mitochondrial respiratory complex inhibitors. J Neurochem. Jul. 2010;114(1):130-41; p. 137, col. 1.

Schumacker, Paul T. Reactive Oxygen Species in Cancer: A Dance with the Devil. Cancer Cell 27, Feb. 9, 2015; pp. 156-157.

Vidale, Simone et al. Postischemic Inflammation in Acute Stroke. J Clin Neurol 2017; 13(1):1-9.

Ye, Fang et al. Efficacy of and Patient Compliance with a Ketogenic Diet in Adults with Intractable Epilepsy: A Meta-Analysis. J Clin Neural 2015; 11(1):26-31.

Fine, Eugene J. et al. Acetoacetate reduces growth and ATP concentration in cancer cell lines which over-express uncoupling protein 2. Cancer Cell International 2009, 9:14.

Stubbs et al., On the Metabolism of Exogenous Ketones in Humans, Frontiers in Physiology, Oct. 30, 2017, vol. 8, Article 848.

Cox et al., Cell Metabolism: Nutritional Ketosis Alters Fuel Preference and Thereby Endurance Performance in Athletes, Aug. 9, 2016, 24, 256-268.

Office Action for Canadian Application No. 2,873,057, dated Oct. 29, 2018 (3 pages).

* cited by examiner

|  | Diabetic Ketoacidosis | Therapeutic Ketosis (ketone ester) |
|---|---|---|
| Blood Ketones (mM) | > 10-20 | 0.5-8 |
| Insulin | Dysregulated/Absent | Low |
| Glycemia | High | Low |
| Renal Metabolism | Ketonuria, glycosuria, reduced GFR | Mild osmotic diuresis |
| Acidosis | Very high | Mild and regulated |
| Pathology | Hypovolemia, hypotension and death | None |
| Cognitive Performance | Impaired | Enhanced |
| Physical Performance | Impaired | Enhanced |

Figure 10 mKE = acetoacetate monoester
dKE = acetoacetate diester
1,3-BD = 1,3-butanediol
BHB Ester = b-hydroxybutyrate ester

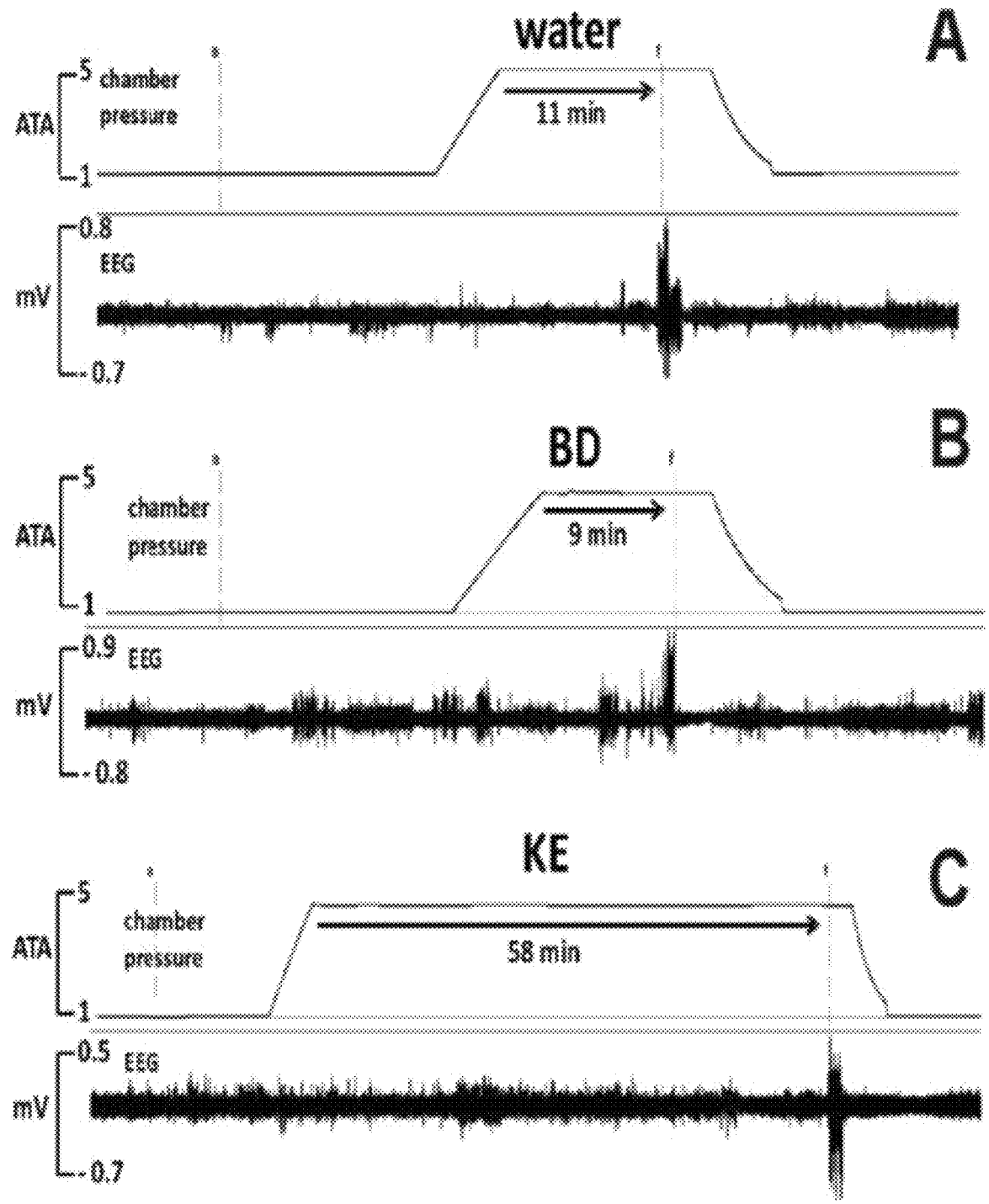
Figure 22A-C

USE OF KETONE ESTERS FOR PREVENTION OF CNS OXYGEN TOXICITY

CROSS REFERENCE TO RELATED APPLICATIONS

This application is a continuation of prior filed International Application, No. PCT/US2012/037099, filed on May 9, 2012, which claims priority to U.S. Provisional Application No. 61/483,927 entitled "The Use of Ketone Esters for Prevention of CNS Oxygen Toxicity", filed May 9, 2011 and U.S. Provisional Application No. 61/579,779 entitled "The Use of Ketone Esters for Prevention of CNS Oxygen Toxicity", filed Dec. 23, 2011, the contents of each of which are hereby incorporated by reference into this disclosure.

STATEMENT OF GOVERNMENT INTEREST

This invention was made with Government support under Grant No. N000140910244, awarded by the Office of Naval Research. The government has certain rights in the invention.

FIELD OF INVENTION

This invention relates to methods of preventing central nervous system oxygen toxicity (CNS-OT). Specifically, the use of ketone esters in the prevention of CNS-OT is presented.

BACKGROUND OF INVENTION

Ketogenic diets (KDs); calorie restriction (CR) and ketogenic precursors (e.g. ketone esters) increase ketone body formation. Ketone bodies represent alternative energy substrates for brain metabolism with anticonvulsant and neuroprotective properties.

It is well known that ketones can replace glucose to supply most of the brain's metabolic energy needs (>50%) during periods of limited glucose availability resulting from starvation, CR or carbohydrate restriction as in KD (Cahill 2006). Moreover, it is known that ketones are a more efficient mitochondrial energy source than glucose (reviewed in Veech, 2004). The invention described below causes a rapid and sustained elevation of blood ketones with a single oral administration. The therapeutic ketosis produced by the invention could reverse the metabolic dysregulation and oxidative stress associated with many neurological disorders.

Cellular Effects of CNS-OT

Hyperbaric oxygen-induced seizures, also known as central nervous system oxygen toxicity (CNS-OT) compromise the safety of undersea divers and patients undergoing $HBO_2$ therapy (HBOT) (Clark and Thom 1997). This condition manifests as tonic-clonic seizures, which carry a significant risk of drowning for divers. Breathing 100% $O_2$ at $P_B$ >2.4 ATA increases the likelihood of seizures in patients, and current applications of HBOT routinely use up to 3 ATA $HBO_2$ (Tibbles and Edelsberg 1996). The potential for CNS-OT is the primary limiting factor in HBOT. CNS-OT occurs with little or no warning and no effective mitigation strategy against it has been identified. Since $HBO_2$ provides a unique, reversible and reproducible stimulus for generalized tonic-clonic seizures in animal models, it is an effective model for assessing the neuroprotective potential of anticonvulsant strategies for epilepsy.

The free radical theory of $O_2$ toxicity predicts the body's antioxidant defenses are overwhelmed by increased production of reactive oxygen species (ROS) (Gerschman, 1954). This theory is supported by the observation that brain levels of ROS and reactive nitrogen species (RNS) increase just prior to $HBO_2$-induced seizures (Demchenko et al. 2003). Other investigators have confirmed ROS is elevated in various brain regions (Piantadosi and Tatro 1990) and in the blood during hyperoxia (Narkowicz et al. 1993).

The inventors have previously shown that caudal solitary complex (SC) neurons and CA1 hippocampal neurons in brain slices are strongly stimulated by pro-oxidants and $HBO_2$ via redox signaling (Dean et al. 2003). In addition, superoxide production and neuronal excitability in the CA1 hippocampus is tightly coupled to tissue $O_2$ concentration ranging from 20-95% (D'Agostino et al. 2007). Using Ethidium Homodimer-1 (EH-1) staining in hippocampal slices, the inventors have shown an $O_2$-dependent increase in cell death of CA1 neurons, with the highest level of cell death observed after 4 hr exposure to 95% $O_2$ (D'Agostino et al. 2007). Evidence suggests that hyperoxia-induced cell death is correlated to mitochondrial function impairment (Li et al. 2004a; Metrailler-Ruchonnet et al. 2007). More specifically, the mitochondrial-dependent cell death involves mitogen-activated protein kinase, proapoptotic Bcl-2 and ultimately mitochondrial depolarization and membrane depolarization (Chandel and Budinger 2007).

Considering the cellular and physiological effects of CNS-OT and the neuroprotective effect of therapeutic ketosis, the inventors induced ketosis as a metabolic strategy to prevent CNS-OT. Ketones may counteract the effects of CNS-OT by a variety of mechanisms, including 1) decreasing ROS production (Kim do et al. 2010); 2) enhancing mitochondrial efficiency (Veech 2004); 3) and acting as a direct anticonvulsant (Gasior et al. 2007; Likhodii et al. 2008).

Therapeutic Ketosis for CNS-OT

Previous studies in rats show that starvation delays the onset of CNS-OT (Bitterman et al. 1997), presumably by fundamentally shifting brain energy metabolism. Starvation (24-36 h) also delays the latency to seizure from $HBO_2$ by up to 300%, which is equally or more effective than high doses of anti-epileptic drugs (AEDs) (Bitterman and Katz 1987; Tzuk-Shina et al. 1991) or than experimental anticonvulsants that block excitatory glutamatergic neurotransmission (Chavko et al. 1998).

During periods of starvation or ketogenic diet (KD) use, the body utilizes energy obtained from free fatty acids (FFA) released from adipose tissue; however, the brain is unable to derive significant energy from FFA (Cahill 2006). Hepatic ketogenesis converts FFAs into the ketone bodies β-hydroxybutyrate (BHB) and acetoacetate (AcAc), and a small percentage of AcAc spontaneously decarboxylates to acetone. During prolonged starvation or KD, large quantities of ketone bodies accumulate in the blood (>5 mM) and are transported across the blood brain barrier (BBB) by monocarboxylic acid transporters (MCT1-4) to fuel brain function, and this ketone transport is enhanced under oxidative stress or limited glucose availability (Prins 2008). The brain derives up to 75% of its energy from ketones when glucose availability is limited (Cahill 2006). Starvation and dietary ketosis are often confused with diabetic ketoacidosis (DKA), but this occurs only in the absence of insulin (VanItallie and Nufert 2003). At least two feedback loops prevent runaway ketoacidosis from occurring, including a ketone-induced release of insulin and ketonuria (Cahill 2006). The metabolic adaptations associated with starvation-induced ketosis improve mitochondrial function, decrease reactive oxygen species (ROS) production, reduce inflammation and increase the activity of neurotrophic factors (Maalouf et al. 2009).

KD mimics the metabolic state associated with starvation (i.e. therapeutic ketosis) and is efficacious in treating drug-resistant seizure disorders (Freeman and Kossoff 2010). This therapeutic method is well established in children and adults (Klein et al. 2010). The anticonvulsant effects of the KD correlate with an elevation of blood ketones, especially AcAc and acetone (Bough and Rho 2007; McNally and Hartman 2011). The KD requires extreme dietary carbohydrate restriction and only modestly increases blood ketones compared to levels associated with prolonged starvation (Cahill 2006). In addition, the unbalanced macronutrient profile of the KD is often considered unpalatable and has the potential to negatively impact lipid profile if consumed in unrestricted amounts (Freeman and Kossoff 2010).

Elevating blood ketones with ketogenic medical foods or exogenous ketones is largely ineffective or problematic for a variety of reasons. Ketogenic fats, like medium chain triglyceride oil (MCT oil) are generally not well tolerated by the gastrointestinal system, and supplementation produces only low levels of ketones (<0.5 mM) (Henderson 2008). Oral administration of BHB and AcAc in their free acid form is expensive and ineffective at producing sustained ketosis. One idea has been to buffer the free acid form of BHB with sodium salts, but this is largely ineffective at preventing seizures in animal models and causes a potentially harmful sodium overload at therapeutic levels of ketosis (Bough and Rho 2007). However, esters of BHB or AcAc can effectively induce a rapid and sustained ketosis (Brunengraber 1997; Desrochers et al. 1995) that mimics the sustained ketosis achieved with a strict KD or prolonged starvation without dietary restriction. Producing esters of BHB or AcAc is expensive and technically challenging, but offers great therapeutic potential (Veech 2004). Orally administered KEs have the potential to induce ketosis and circumvent the problems associated with starvation-induced or diet-induced ketosis.

The KE that the inventors have synthesized and tested, R,S-1,3-butanediol acetoacetate diester (BD-AcAc$_2$), has been shown to induce therapeutic ketosis in dogs (Ciraolo et al. 1995; Puchowicz et al. 2000) and pigs (Desrochers et al. 1995) and was proposed as a metabolic therapy for parenteral and enteral nutrition (Brunengraber 1997). The inventors were interested in esters of AcAc because precursors to BHB do not prevent CNS-OT (Chavko et al. 1999), and animal studies suggest that AcAc and acetone have the greatest anticonvulsant potential (Bough and Rho 2007; Gasior et al. 2007; Likhodii et al. 2003; McNally and Hartman 2011).

Anticonvulsant Mechanisms of Ketogenesis

The anticonvulsant mechanism the KD is largely unknown (Bough and Rho 2007). Proposed mechanisms for the anticonvulsant effect include, but are not limited to, decreased blood glucose, increased inhibitory neuromodulators, diminished excitatory neurotransmission and enhanced mitochondrial function by ketones (Greene et al. 2003; Hartman et al. 2007; Jahn 2010; Masino et al. 2009). The anticonvulsant mechanism of the KD is of great importance for those involved in developing anti-seizure therapies. There exists an intense interest to develop a substance that produces a rapid, safe and sustained elevation of blood ketones for prevention of seizures, a "ketogenic diet in a pill" (Rho and Sankar 2008). Ketone administration (independent from the KD) may directly mediate anticonvulsant effects by virtue of acetoacetate (AcAc) decarboxylating to acetone, a lipophilic solvent with strong anticonvulsant effects (Bough and Rho 2007; Likhodii et al. 2008). In addition, ketones may prevent synaptic dysfunction by preserving mitochondrial metabolism, reducing ROS (Kim do et al. 2010) and supplying an alternative form of energy with a higher $\Delta G'$ value of ATP hydrolysis (Veech 2004).

Evidence for the KD working through novel ketone-induced mechanisms is supported by the fact that the KD works when even high doses of multiple antiepileptic drugs (AEDs) fail (Kim do and Rho 2008). Thus, the KD activates mechanisms other than those targeted by any specific AED, or even combinations of AEDs. Surprisingly, no commercially available AEDs attempt to mimic therapeutic ketosis conferred by the KD. However, evidence suggests that a common ketogenic precursor (MCT oil) induces a very mild ketosis that confers anticonvulsant effects (Neal et al. 2009) and improves mild cognitive impairment in patients by (Henderson 2008). Interestingly, inducing ketosis by administration of the primary ketone, beta-hydroxybutyrate (BHB), or BHB precursors does not prevent acutely provoked seizures in animal models (Bough and Rho 2007) including CNS-OT (Chavko et al. 1999). In contrast, elevation of Acc and acetone prevents acutely provoked seizures (chemical, electrical) in animal models (Likhodii et al. 2008; Rho et al. 2002; Yamashita 1976) including CNS-OT (Chavko et al. 1999). Acetone is relatively nontoxic (LD50>5 g/kg; rat) and anticonvulsant at subnarcotic concentrations (Gasior et al. 2007; Likhodii et al. 2003) and its anticonvulsant effect is due to its membrane stabilizing lipophilic properties. Taken together, these observations suggest that methods of therapeutic ketosis for treatment of CNS $O_2$ toxicity and seizures should be designed to elevate AcAc, which is typically in a 1:4 ratio with BHB.

Antioxidant Effects of Ketones

The neuroprotective effects of ketone bodies may be linked to their antioxidant effects. Glutamate-induced ROS production is inhibited by ketone bodies in primary cultures of rat neocortical neurons (Maalouf et al. 2007). Recently it's been shown that diet-induced ketogenesis improves mitochondrial redox state via the transcription factor Nrf2 (Milder and Patel 2011; Milder et al. 2010), which is considered the "hub" of endogenous antioxidant regulation. Ketone bodies also protect against cell death and impairment of long term potentiation after neocortical slices are exposed to hydrogen peroxide (Maalouf et al. 2009). In addition to effects on neurotransmission, ketones may prevent synaptic dysfunction by reducing ROS and preserving brain metabolism during metabolic or oxidative stress (Kim do et al. 2010; Veech 2004).

The present invention provides a mitigation strategy against CNS-OT seizures using ketone ester-induced therapeutic ketosis. The inventors found that oral administration of R,S-1,3-butanediol acetoacetate diester (BD-AcAc$_2$) mimics the anticonvulsant effect of starvation-induced ketosis and delays the onset of CNS-OT.

SUMMARY OF INVENTION

Central nervous system oxygen toxicity (CNS-OT) seizures occur with little or no warning, and no effective mitigation strategy has been identified. Ketogenic diets (KD) elevate blood ketones and have successfully treated drug-resistant epilepsy. The inventors administered a ketone ester (KE) orally as a non-ionized precursor of acetoacetate (AcAc), R,S-1,3-butanediol acetoacetate diester (BD-AcAc$_2$) to delay seizures in rats breathing hyperbaric oxygen (HBO$_2$) at 5 atmospheres absolute (ATA). KE was found to cause a rapid and sustained (>4 h) elevation of BHB (>3 mM) and AcAc (>3 mM), which exceeded values reported with a KD or starvation. KE increased the latency to seizure (LS) by 574±116% compared to control (water), and was due to the effect of AcAc and acetone, but not BHB. BD produced ketosis in rats by elevating BHB (>5 mM), but AcAc and acetone remained low or undetectable. BD did not increase LS. It was found that acute oral administration of KE produced sustained therapeutic ketosis and significantly delayed CNS-OT by elevating AcAc and acetone. KE represents a novel therapeutic mitigation strategy for CNS-OT and seizure disorders, especially AED-resistant seizures.

In an embodiment, a method of treating neurological disorders arising from impaired brain metabolism is presented comprising inducing mild ketosis by administering a therapeutically effective dose of a ketone ester whereby administration of the ketone ester elevates blood ketone levels and maintains the therapeutic ketosis for several hours. The ketone ester may be derived from acetoacetate (AcAc). The ketone ester may be a R,S-1,3-butanediol acetoacetate ester such as R,S-1,3-butanediol acetoacetate monoester (BD-AcAc), R,S-1,3-butanediol acetoacetate diester (BD-AcAc$_2$), or a combination of (BD-AcAc) and (BD-AcAc$_2$). The neurological disorder may be selected from the group consisting of seizure disorders, brain cancer and Alzheimer's disease.

In a further embodiment, a method of protecting against hyperoxia-induced oxidative stress is presented comprising inducing mild ketosis by administering a therapeutically effective dose of a ketone ester at a predetermined time period whereby administration of the ketone ester elevates blood ketone levels and maintains the elevated level for several hours. The ketone ester may be BD-AcAc, BD-AcAc$_2$, or a combination of BD-AcAc and BD-AcAc$_2$. The ketone ester may be administered at least 30 minutes prior to potential HBO$_2$ exposure.

In another embodiment, a method of protecting against central nervous system oxygen toxicity (CNS-OT) is presented comprising inducing mild ketosis by administering a therapeutically effective dose of a ketone ester at a predetermined time period whereby administration of the ketone ester elevates blood ketone levels and maintains the elevated level for several hours. The ketone ester may be BD-AcAc, BD-AcAc$_2$, or a combination of BD-AcAc and BD-AcAc$_2$. The ketone ester may be administered at least 30 minutes prior to potential hyperbaric oxygen (HBO$_2$) exposure.

BRIEF DESCRIPTION OF THE DRAWINGS

For a fuller understanding of the invention, reference should be made to the following detailed description, taken in connection with the accompanying drawings, in which:

FIG. 10 is a table depicting the comparison of ketogenesis from starvation, ketogenic diet, ketone ester with the pathological state of diabetic ketoacidosis (DKA) and alcoholic ketoacidosis (AKA).

DETAILED DESCRIPTION OF THE PREFERRED EMBODIMENTS

Figure 1:
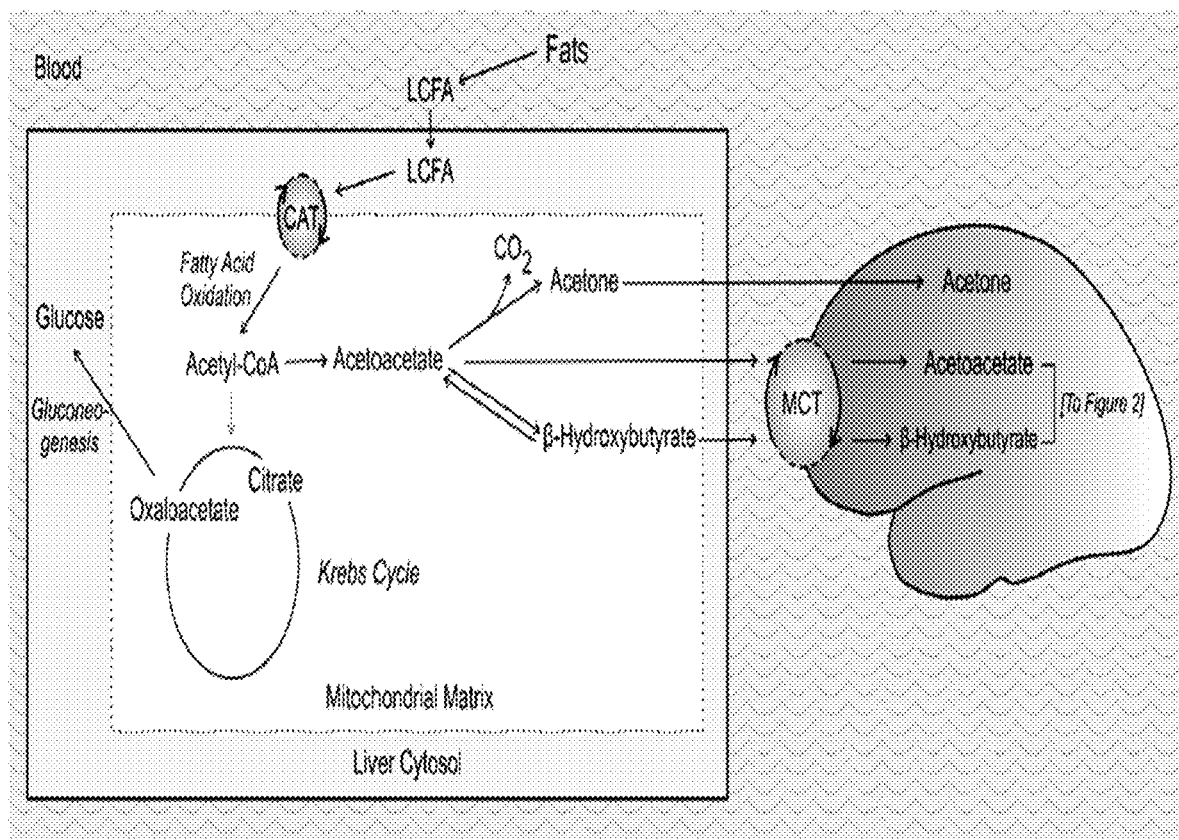
FIG. 1 is an image depicting that acetone readily crosses the BBB whereas acetoacetate and B-hydroxybutyrate are transported via the monocarboxylic acid transporter (MCT). (Hartman et al. *Pediatric Neurology.* 2007 May; 36(5): 281-292)

In the following detailed description of preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

As used in the specification and claims, the singular form "a", "an" and "the" includes plural references unless the context clearly dictates otherwise.

"Patient" is used to describe an animal, preferably a human, to whom treatment is administered, including prophylactic treatment with the compositions of the present invention. "Patient" and "subject" are used interchangeably herein.

"Ketosis" as used herein refers to an increase in ketone bodies in a subject. Ketosis may improve mitochondrial function, decrease reactive oxygen species (ROS) production, reduce inflammation and increase the activity of neurotrophic factors. Ketosis is safe at levels below about 8 mM and these levels are referred to herein as a nonpathological "mild ketosis" or "therapeutic ketosis". Ketosis may be due to a ketogenic diet (KD), starvation, or the administration of supplemental ketones.

The term "neurological disorders" as used herein refers to disorders of the central nervous system that are caused by disruptions of brain metabolism. These neurological disorders include, but are not limited to, seizure disorders, Alzheimer's disease, malignant brain cancer including glioblastomas, and traumatic brain injury.

The term "cancer", "tumor", "cancerous", and malignant" as used herein, refer to the physiological condition in mammals that is typically characterized by unregulated cell growth. Examples of cancer include, but are not limited to, brain cancer including tumors in neural tissue such as gliomas, glioblastomas, neuroblastomas, neuroepitheliomatous tumors, and nerve sheath tumors.

"Administration" or "administering" is used to describe the process in which individual ketone esters or any combination of ketone esters thereof of the present invention are delivered to a subject. The composition may be administered in various ways including oral, intragastric, and parenteral (referring to intravenous and intra-arterial and other appropriate parenteral routes), among others. Each of these conditions may be readily treated using other administration routes of ketone esters or any combination thereof to treat a disease or condition.

The "therapeutically effective amount" for purposes herein is thus determined by such considerations as are known in the art. A therapeutically effective amount of individual ketone esters or any combination thereof is that amount necessary to provide a therapeutically effective result in vivo. The amount of ketone esters or any combination of ketone esters thereof must be effective to achieve a response, including but not limited to total prevention of (e.g., protection against) and to improved survival rate or more rapid recovery, or improvement or elimination of symptoms associated with seizure disorders, neurological disorders, cancer or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

The amount of the ketone ester will depend on absorption, distribution, metabolism, and excretion rates of the ketone ester as well as other factors known to those of skill in the art. Dosage values may also vary with the severity of the condition to be alleviated. The compounds may be administered once, or may be divided and administered over intervals of time. It is to be understood that administration may be adjusted according to individual need and professional judgment of a person administrating or supervising the administration of the compounds used in the present invention.

The dose of the ketone esters administered to a subject may vary with the particular ketone ester, the method of administration, and the particular disorder being treated. The dose should be sufficient to affect a desirable response, such as a therapeutic or prophylactic response against a particular disorder or condition.

CNS oxygen toxicity (CNS-OT) is a condition resulting from the harmful effects of breathing molecular oxygen ($O_2$) at elevated partial pressures, which is known to generate ROS and disrupt brain energy metabolism, which triggers a tonic-clonic seizure. Ketogenesis can be used as a therapeutic strategy to preserve brain metabolism and decrease ROS production in response to toxic levels of hyperbaric oxygen (HBO). Therapeutic ketosis can also be used for a wide range of neuropathologies resulting from impaired energy metabolism, impaired glucose utilization and elevated levels of oxidative stress.

The etiology of CNS-OT is unknown, but the general consensus is that hyperoxia-induced seizures are triggered by an overproduction of ROS, which disrupts metabolic and ultimately leads to neuronal dysfunction. Therapeutic ketosis may counteract the effects of CNS-OT by a variety of mechanisms, including 1) decreasing ROS production, 2) enhanced mitochondrial efficiency, 3) and by a direct anticonvulsant effect of specific ketones like acetone. Metabolic studies are being done to determine the precise mechanism of ketone-induced neuroprotection.

Induction of mild ketosis from caloric restriction or the ketogenic diet confers neuroprotection against a wide range of pathologies. Interestingly, the brain's ability to use exogenous ketone bodies for fuel has not been exploited therapeutically. The inventors found that exogenous ketones prevent hyperbaric oxygen-induced seizures in rats, reduce Aβ-induced oxidative stress in cultured neurons and impair proliferation of brain cancer cells. Results demonstrate that a single intragastric administration of ketone ester in rats (n=12) confers protection from CNS oxygen toxicity (5 ATA $O_2$) by delaying the latency to seizure from about 16.4±5 minutes (control) to about 79.3 minutes (10 g/kg ketone ester).

Studies of primary cultured cortex neurons fluorescence microscopy with dihydroethidium confirmed that superoxide anion production (measured as DHE fluorescence units) decreased significantly with ketone treatment (2 mM ketones). Superoxide anion production was 27% lower in hyperoxia-treated cultures and 24% lower in Aβ-42 treated cultures. Ketone treatment in brain cancer cells (U87MG cultures) significantly reduced cell proliferation (39%) and viability, as assessed by ethidium homodimer-1 staining The inventors found that 1) oral administration of ketone ester is neuroprotective against seizures resulting from CNS-OT in rats, 2) supplemental ketones reduce superoxide production in cultured cortex neurons exposed to hyperbaric oxygen and Aβ-42, and 3) ketones decrease proliferation and viability in U87 glioma. These observations support the therapeutic effect of ketones for neurological disorders such as seizure disorders, Alzheimer's disease and malignant brain cancer.

As described above, KD has a profound neuroprotective and anticonvulsant effect and is used in children to treat drug-resistant epilepsy. The literature suggests that the anticonvulsant effect of the KD depends on an elevation of a specific blood ketone (AcAc), but that βHB also provides unique neuroprotective properties. A dietary supplement of ketone esters can rapidly elevate blood ketones and significantly maintain elevated ketone levels for several hours, even higher than levels achieved with fasting, CR or KD, and without fear of metabolic acidosis associated with diabetic ketoacidosis (DKA).

The invention presented herein details the neuroprotective and anticonvulsant effect of ketone esters against CNS-OT (seizures). More specifically, it has been found that a single dose of ketone ester formulas including BD-AcAc and R BD-AcAc$_2$, can dramatically increase resistance to seizures (i.e. latency time to seizure) in rats exposed to hyperbaric oxygen (HBO$_2$; 5 ATA $O_2$). In addition, supplemental ketone administration prevents hyperoxia-induced oxidative stress (superoxide anion production) in cultured cortical neurons. Currently, there is no commercially-available food product or pharmaceutical that elevates ketones as significantly as ketone esters.

The inventors developed ketone esters from esters of acetoacetate (AcAc) because precursors to B-hydroxybutyrate (BHB) do not prevent CNS-OT (Chavko et al. 1999), and animal studies suggest that AcAc and acetone have the greatest anticonvulsant potential (Bough and Rho, 2007; Gasior et al., 2007; Likhodii et al., 2003; McNally and Hartman, 2011)

The inventors developed specific esters, including an enriched BD-AcAc and a purified form of BD-AcAc$_2$. These esters can be used alone or in mixtures. BD-AcAc is relatively water soluble, whereas BD-AcAc$_2$ is poorly water soluble and lipophilic.

The BD-AcAc and BD-AcAc$_2$ are non-ionized sodium-free precursors of the ketone body acetoacetate. When ingested these KEs are de-esterified in the blood and tissues by esterase enzymes and release acetoacetate in a rapid and sustained process. The resulting R,S-1,3 butanediol is a common food additive that breaks down to β-hydroxybutyrate. The metabolic fate of R,S-1,3 butanediol involves alcohol dehydrogenase, which catalyses the initial step in metabolism of 1,3-butanediol to β-hydroxybutyraldehyde, which is rapidly oxidized to β-hydroxybutyrate by aldehyde dehydrogenase. Subsequent metabolic steps to acetoacetate and acetyl CoA supplies substrate for the Krebs cycle (tricarboxylic-acid cycle) to produce carbon dioxide and reducing equivalents (that are converted to ATP by the electron transport chain).

Materials and Methods

Animal and Surgical Procedures

All animal procedures were done in accordance with the University of South Florida Institutional Animal Care and Use Committee (IACUC) guidelines. Adult male Sprague-Dawley rats (n=60), 250-300 grams, were obtained from Harlan, anesthetized in 3-5% isoflurane (in $O_2$) and implanted with a 4ET radio-transmitter (Data Sciences International, DSI) using sterile surgical technique. One pair of leads (positive and negative poles) was implanted in the costal diaphragm at the junction with the abdominal wall for diaphragmatic electromyogram (dEMG) signals, one pair of electrodes was inserted in the pectoral muscle to acquire electrocardiogram (ECG) data, and two pairs of wires were embedded in the skull between Bregma and Lambda, with one lead on either side of midline for each pair (EEG recordings). The EMG wires were not inserted into crural diaphragmatic muscle because of the high risk of pneumothorax due to the thinness of the muscle (419 to 630 μm). 4ET radio-transmitters also monitored core body temperature and physical activity. Rats were weighed immediately before surgery and subsequently once every 7 days, just prior to the weekly exposures to $HBO_2$. After surgery, every animal recovered for ≥1 week.

Hyperbaric Radio Telemetry

The radiotelemetry system consisted of an implantable 4ET radio-transmitter able to amplify and broadcast signals via a receiver (DSI PhysioTel, model RPC-2) connected to an acquisition interface unit (ACQ 7700 Ponemah) via electrical penetrations in the wall of the hyperbaric chamber. The acquisition interface unit was connected to a computer for real time data collection and storage. The same acquisition unit also recorded chamber pressure and temperature, which were measured, respectively, by a thermocouple and pressure gauge directly connected to the acquisition system via BNC (Bayonet Neill-Concelman) cables. Each animal was continuously monitored via a video camera (AXIS 221 Network Camera) and the video of each experiment was recorded as well.

Acquisition/Analysis Software

Raw data was collected using DSI Ponemah software (P3 Ponemah Physiology Platform, version 4.90). Statistical analysis was performed using GraphPad PRISM®, version 3.03.

Hyperbaric Chamber $HBO_2$ Protocol

The hyperbaric system consisted of two main elements: 1) a plexiglass chamber (~3 liter capacity, Diamond Box, Buxco, Electronics Inc., model PLY3114), that housed the rat during the experiment, and 2) a hyperbaric chamber (Reimers System Inc.—7.8 ATA MWP), that contained the plexiglass chamber and functioned as the pressure vessel. Both chambers were connected to an air compressor (oil-less rotary scroll compressor—model DK6086, Powerex).

$HBO_2$ Exposures (Dive Profile)

During each experiment (hyperbaric hyperoxia), both the main chamber and the animal chamber were filled with air. Rats were placed into the plexiglass chamber and allowed ten minutes to acclimate, at which time the plexiglass chamber was flushed with 100% $O_2$. The animal was then allowed 15 minutes to acclimate before both chambers were compressed to 5 ATA (58.8 PSIG) at a rate of 0.7 ATA/min. The outer chamber was pressurized using air (capacity ~205 liters) to minimize the risk of an electrical-induced fire. Each experiment was visually monitored via a live camera. LS was calculated from the moment at which the internal and the external chambers reached 5 ATA until the onset of convulsions, identified as high-amplitude, high frequency spikes lasting 10 to 30 sec, followed by polyspikes and wave formation concurrent with tonic-clonic motions of forelimbs and head. After the onset of seizures, the plexiglass chamber was flushed with air to quickly terminate seizure, and both chambers decompressed to sea level. Decompression rate was 1 ATA/min. Rats were then allowed a 15 min recovery period in air at 1 ATA before being removed from the chamber.

Synthesis of Ketone Esters

R,S-1,3-butanediol and t-butylacetoacetate were purchased from Sigma (Milwaukee, Wis., USA). All commercial solvents and reagents used were high-purity reagent-grade materials. The KEs synthesized, R,S-1,3-butanediol acetoacetate (BD-AcAc) and R,S-1,3-butanediol acetoacetate diester (BD-AcAc$_2$), are a non-ionized sodium-free and pH-neutral precursors of AcAc. KEs were synthesized by transesterification of t-butylacetoacetate with R,S-1,3-butanediol (Savind Inc., Seymour, Ill.). The resultant product consisted of a mixture of monoesters and diester, the ratio of which could be adjusted by varying the stoichiometry of reactants. Following synthesis the crude product was distilled under reduced pressure to remove all solvents and starting materials, and the resultant BD-AcAc or BD-AcAc$_2$ was obtained and assessed for purity using gas chromatography-mass spectrometry (GC-MS).

Measurement And Analysis of Blood Glucose, Ketones, Gases and pH

To determine the time course of ketosis, 18 adult male Sprague-Dawley rats (250-350 grams), pathogen-free, were purchased from a vendor (Harlan) and shipped 7 days after being implanted with carotid catheters. The rats were food (not water) deprived for 18 hours prior to the start of the experiment. Test substances of distilled water (control), BD (10 g/kg) or BD-AcAc$_2$ (10 g/kg) were administered by 3 ml oral gavage (this was time 0). Whole blood samples (10 μl) were acquired for analysis of glucose and BHB at USF utilizing a commercially available glucose/ketone monitoring system (Nova Max® Plus) at time 0, 30, 60, 120, 180 and 240 min. In addition, heparinized blood samples (200

μl) were collected into Eppendorf tubes at time 0, 30, 60, 120, 180 and 240 min. Samples were processed for the detection and quantification of BHB, AcAc, and acetone at Case Western Reserve University, Mouse Metabolic Phenotyping Center (MMPC). Briefly, samples were chilled on ice for 30 s, centrifuged in a micro-centrifuge (13,000 G) for 3-5 min and plasma (>100 μl), treated with reducing reagent of cold 0.2M sodium borodeuteride ($NaBD_4$; Sigma, 205591, CAS 15681-89-7) dissolved in 0.1M NaOH (8.4 mg $NaBD_4$ in 1 ml of 0.1M NaOH) and then immediately frozen on dry ice before storing at −80° C. Acetone was analyzed at the 60 minute time point, which was the predicted peak of blood AcAc levels (Desrochers et al. 1995). 300 μl of whole blood were collected in addition to the above collections, stabilized with cold 0.2M $NaBD_4$, and then immediately frozen on dry ice. Samples were stored at −80° C. until analyzed for ketones. Internal standards of [$^2H_6$]BHB or [$^2H_8$]isopropanol were added to the treated plasma or blood samples (50 μl or 15 μl) and the BHB, AcAc (as M+1 of BHB) or acetone (as 2-propanol) metabolites were analyzed by gas chromatography-mass spectrometry (GC-MS) using an Agilent 5973 mass spectrometer, linked to a 6890 gas chromatograph equipped with an autosampler. Briefly, GC-MS conditions were either EI or CI mode (electron or chemical ionization mode); the samples were detected by selected ion monitoring as the BHB- and AcAc-trimethylsilyl derivatives (EI) or the derivative of acetone-pentafluorobenzoyl (CI).

In addition, a 60 μl blood sample was withdrawn at each time point and immediately analyzed with a blood gas analyzer (OPTI CCA-TS© Blood Gas Analyzer, cat #: GD7013-Global Medical Instrumentation, Inc.) for blood pH, $pO_2$, and $pCO_2$.

Cell Culture

Primary dissociated neuronal cultures of the hippocampus and cortex are acquired from Brain Bits LLC, to increase time efficiency and to minimize cost associated with purchasing rats. Hippocampal or cortical tissue from Brain Bits (shipped in Hibernate®) are enzymatically and mechanically dissociated via pipette trituration. Neurons are plated on 12 mm glass coverslips and allowed to adhere for 1-2 hrs in an incubator maintained at 9-20% $O_2$ in a humidified atmosphere. Cultures are maintained in media purchased from Brain Bits, including NbActiv1® and NbActive4. After incubation for 7 to 21 days the neurons are placed in the cell chamber on the stage of the hyperbaric imaging system and gently superfused (0.5 ml/min) with aCSF equilibrated with the test level of $O_2$. For experimental protocols cell cultures are maintained in artificial cerebrospinal fluid (aCSF in mM: 125 NaCl, 3.5 KCl, 1 $CaCl_2$, 1 $MgCl_2$, 24 $NaHCO_3$, 0.6 $NaH_2PO_4$, and 15 glucose) equilibrated with a range of $O_2$ levels (from 0.09 to 5.0 $ATAO_2$).

Fluorescent probes (for use with fluorescence and confocal microscopy)

List of fluorescence probes that will be purchased from Invitrogen:

Dihydroethidium, DHE (1-10 μM; Exλ 525, Emλ 590) detects intracellular $\cdot O_2^-$ generation (Bindokas et al. 1996; D'Agostino et al. 2007).

Calcein-AM (4 μM; Exλ 490, Emλ 535) detects cell volume and monitors cell viability (Crowe, 1995; Inglefield, 1998; Inglefield, 1999).

Ethidium Homodimer-1, EH-1 (6 μM; Exλ 525, Emλ 590) enters cells upon membrane damage and thus labels dead or dying cells (Bickler and Hansen 1998; Pinheiro et al. 2006).

Fluorescence and Confocal Microscopy

Acquisition and statistical analyses of fluorescence imaging was performed as previously reported (D'Agostino, 2007; Filosa, 2002; Ritucci, 1996; Ritucci, 1997; Ritucci, 1998; Crowe, 1995; Weinlich, 1998; Inglefield, 1998; Inglefield, 1999). Average fluorescence intensity (FI) for each cell is calculated as the percent change in fluorescence from baseline, $\Delta FI=(1-FI/FI_b)\times 100$, where $FI_b$ is the basal fluorescence defined by the two images preceding the experimental recordings. Each cell serves as its own control. Statistical differences between control data and hyperoxic data are tested using ANOVA and the appropriate multiple comparisons post hoc test (P<0.05). All FI values are reported as the mean±SEM. Differences between measured values or between groups are determined using the Student's t-test analysis at the P<0.05 significance level.

Detecting ROS by DHE in Fluorescence Microscopy and Spectrophotometry

Presence of intracellular ROS is measured by detection of superoxide anion using Dihydroethidium (DHE). Cells are exposed to $HBO_2$ (5 ATA $O_2$). Following treatment, cells are incubated in 5 μM DHE for 10 minutes in the dark. DHE is permeable to the cell membrane and freely enters the cell where it reacts with superoxide anion to produce the oxidized ethidium. Ethidium intercalates into the DNA and fluoresces red with an excitation/emission of 485/515 nm. Cells are washed in PBS and then visualized using fluorescent microscopy or quantified using spectrophotometry.

Detecting Cell Viability Identification Using the LIVE/DEAD Viability/Cytotoxicity Kit for Mammalian Cells by Invitrogen.

The ratio of live to dead cells was measured using the LIVE/DEAD Viability/Cytotoxicity Kit for Mammalian Cells (Invitrogen). Cells are grown to desired density on a coverslip and washed with Dulbecco's phosphate-buffered saline (D-PBS). Cells were then exposed to $HBO_2$ (5 ATA $O_2$). The LIVE/DEAD reagent is applied and cells are incubated for 30 minutes at room temperature. The cells were washed with D-PBS and the wet coverslip is mounted on the microscope slide. The two-color fluorescence assay contains two probes which specifically label live or dead cells. Live cells possess ubiquitous intracellular esterases which cleave the non-fluorescent calcein AM into the highly fluorescent calcein. Calcein produces an intense green fluorescence with an excitation/emission of 495/515 nm. Ethidium homodimer-1 (Ethd-1) only enters with damaged membranes and binds to nucleic acid. Ethd-1 bound to DNA produces a red fluorescence in dead cells with an excitation/emission of 495/635 nm. Live and dead cells are identified and quantified using standard fluorescent microscopy.

The following examples provide evidence for the use of supplemental ketone esters in providing neuroprotective effects for brain cancer, Alzheimer's disease and seizure disorders.

EXAMPLE 1

Neuroprotective Effect of Supplemental Ketones

Ketogenic diets (KDs), calorie restriction (CR) and ketogenic precursors (e.g. ketone esters) increase ketone body formation. Ketone bodies represent alternative energy substrates for brain metabolism with anticonvulsant and neuroprotective properties. Acetone readily crosses the blood brain barrier (BBB), whereas acetoacetate and B-hydroxybutyrate are transported via the monocarboxylic acid transporter (MCT) as illustrated in FIG. 1.

Figure 2A:
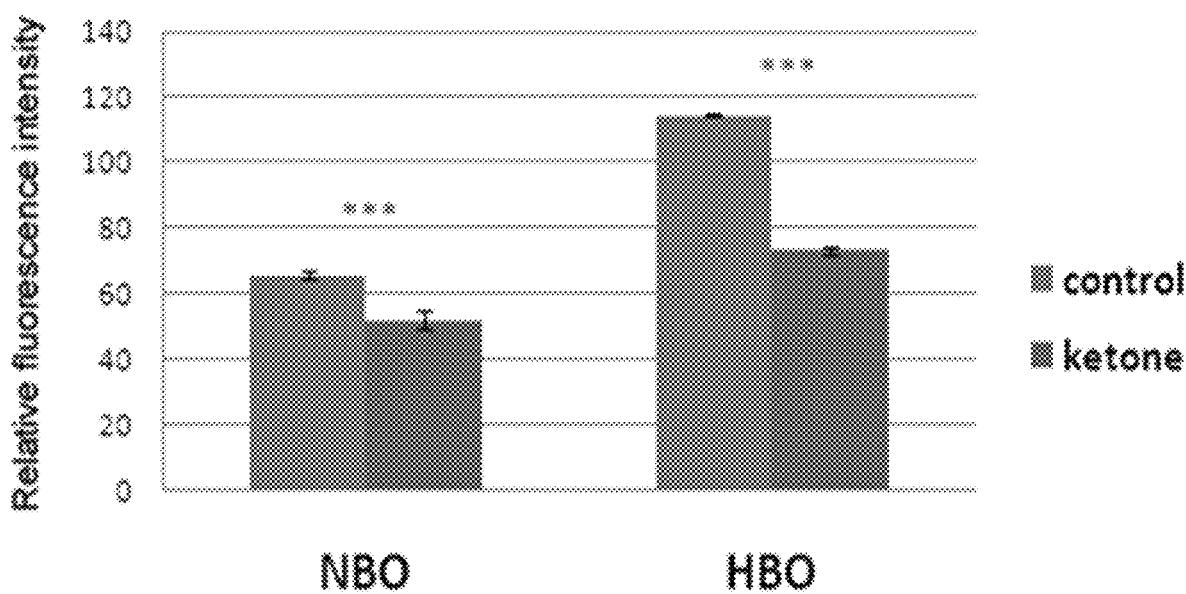
FIG. 2 is a series of images depicting the effect of ketones superoxide production (dihydroethidium fluorescence; DHE) in neurons treated with Aβ42 and HBO and on cell viability of U87MG cells (cancer cells). (A) Superoxide anion production was significantly lower in ketone treated cells under normobaric pressure (NBO) and hyperbaric pressure (HBO); (B) In case of Aβ42 treated cells a significant reduction of ROS production was observed in NBO and HBO groups treated with ketones. (n=12 cultures/group; *, P<0.05). (C) The total number of dead (ethidium homodimer-1) U87 cells was similar between groups, but the percentage of live (calcein) cancer cells significantly decreased in ketone-treated (2 mM ketones) cultures. (n=30 culture dishes/group; *, P<0.05).
Figure 2B:
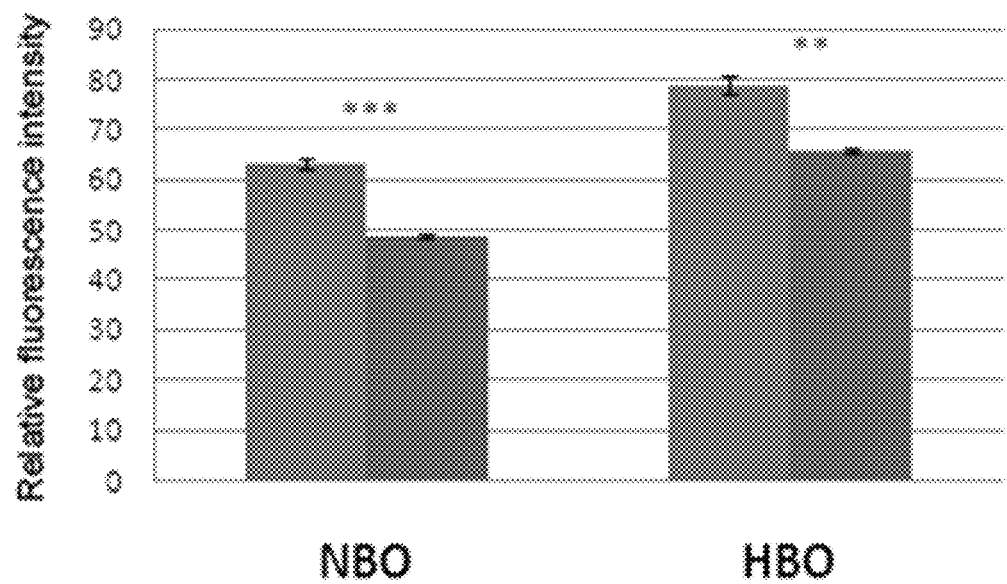
Figure 2C:
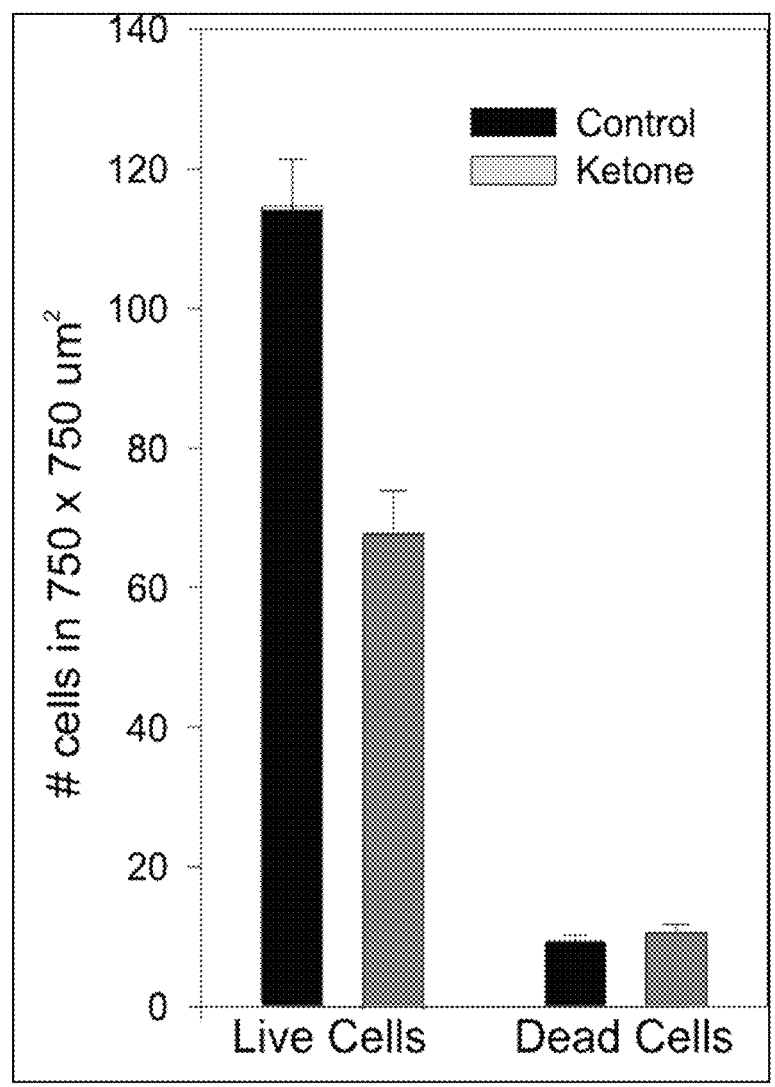

Neuroprotective Effect of Supplemental Ketones on Neuronal Production of Superoxide and Viability of U87MG Cancer Cells Effect of ketones on superoxide production in neurons treated with Aβ42 and HBO and cell viability of U87MG cells is shown in FIG. 2A-C. FIG. 2A shows superoxide anion production was significantly lower in ketone treated cells under normobaric pressure (NBO) and hyperbaric pressure (HBO). FIG. 2B shows that in the case of Aβ42 treated cells a significant reduction of ROS production was observed in NBO and HBO groups treated with ketones. FIG. 2C shows the total number of dead (ethidium homodimer-1) U87 cells was similar between groups, but the percentage of live (calcein) cancer cells significantly decreased in ketone-treated (2 mM ketones) cultures. (n=30 culture dishes/group; *, P<0.05). These results implicate the applicability of supplemental ketones as a therapy for neurological disorders in which Aβ is implicated such as Alzheimer's disease. Ketones protect neurons from oxidative stress, but increase cell death in cancer cells, which cannot use ketones as a metabolic fuel due to defective mitochondria.

In studies of primary cultured cortex neurons fluorescence microscopy with dihydroethidium confirmed that superoxide anion production (measured as DHE fluorescence units) decreased significantly with ketone treatment (2 mM ketones). Superoxide anion production was 27% lower in hyperoxia-treated cultures and 24% lower in Aβ-42 treated cultures. Ketone treatment in brain cancer cells (U87MG cultures) significantly reduced cell proliferation (39%) and viability, assessed with ethidium homodimer-1 staining. These results implicate the applicability of supplemental ketones as a potential therapy for brain cancer.

Figure 3:
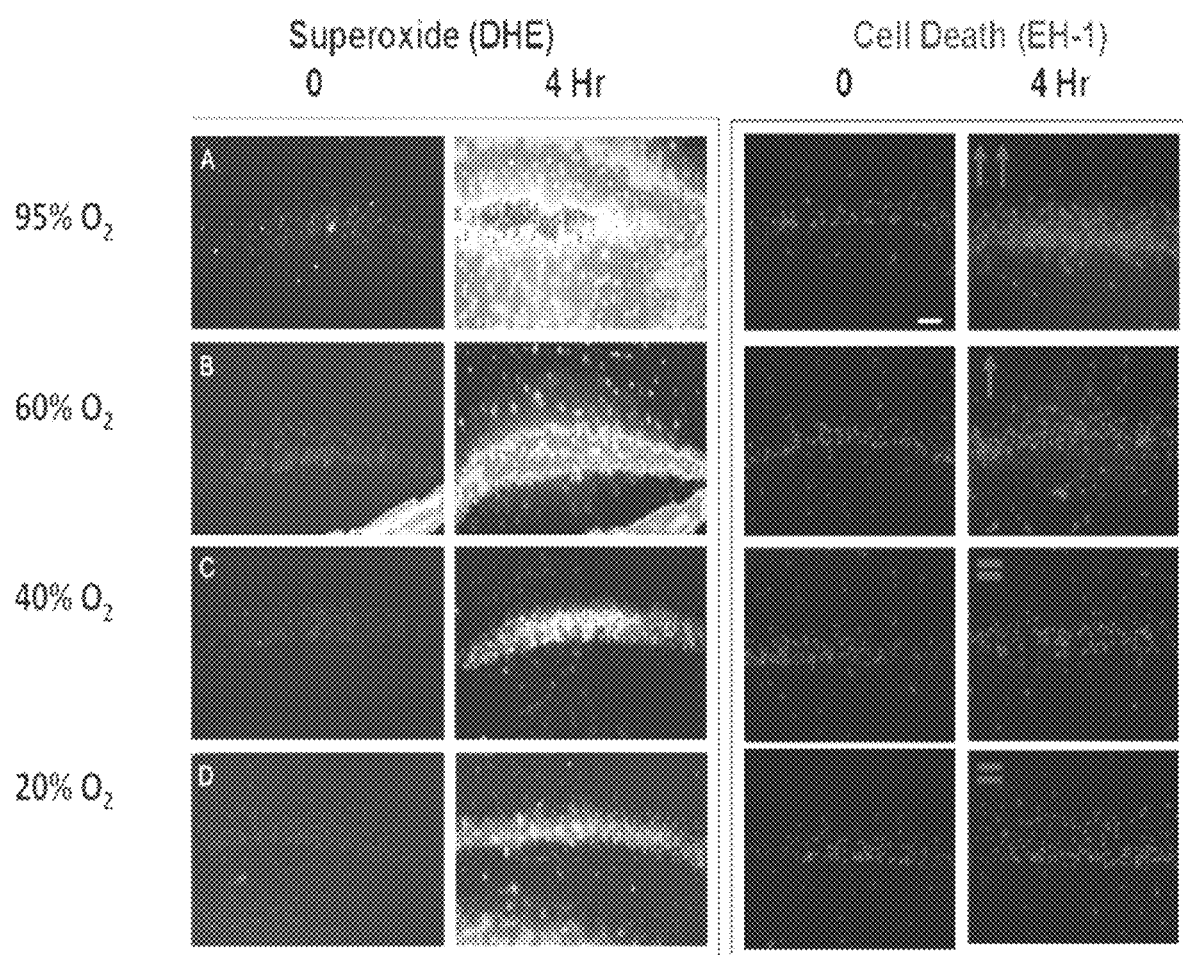
FIG. 3 is an image depicting superoxide production (DHE fluorescence) in the CA1 region of a hippocampal brain slice preparation exposed to graded levels of oxygen over 4 hours. Note the oxygen-dependent increase in superoxide production. Hyperoxia-induced superoxide production was associated with increased cell death (ethidium homodimer-1 staining) (D'Agostino et. al)
Figure 4:
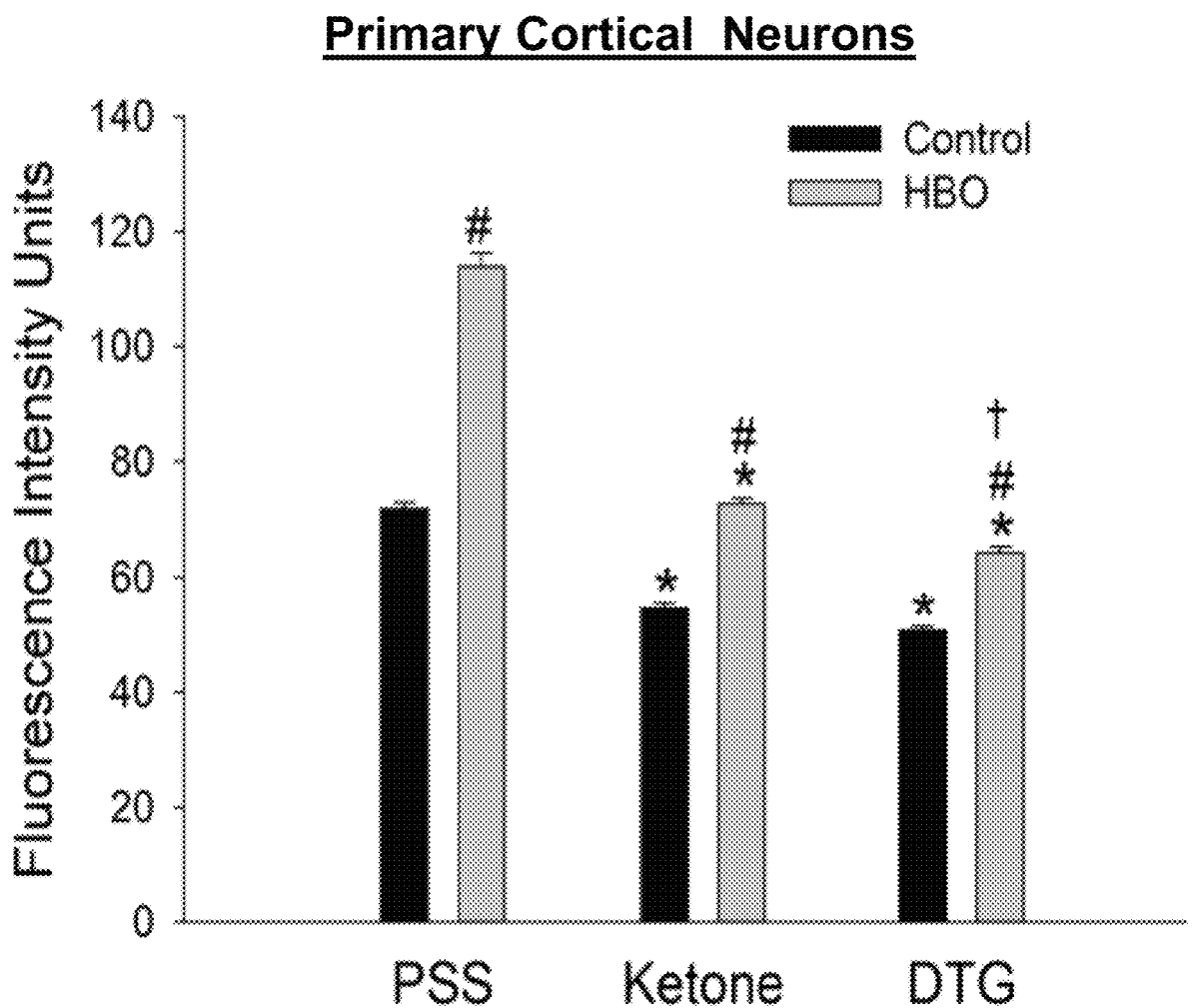
FIG. 4 is an image depicting the effect of ketones (2 mM ketones) and a sigma receptor agonist, 1,3,-di-o-tolylguanidine (DTG), on superoxide anion production (DHE fluorescence) in primary cultures of rat cortical neurons under control conditions and hyperbaric oxygen (5 ATA O$_2$). Primary cortex neurons grown for 10 days under normal conditions were exposed to acute hyperoxia (60 min, 5 ATA O$_2$). HBO$_2$ caused a significant increase in superoxide anion production in cells. Ketone treatment decreased baseline superoxide production in a way that resembled the effect of the neuroprotective drug DTG. Both ketones and DTG prevented the hyperoxia-induced increase in superoxide production (n=110 cells analyzed/condition, * indicates p≤0.005).

Neuroprotective Effects of Supplemental Ketones in Cortex and Hippocampal Neurons Brain images illustrating superoxide production in CA1 division of hippocampus exposed to graded levels of oxygen are shown in FIG. 3. Ketones were found to protect cells from hyperoxia-induced oxidative stress as shown in FIG. 4. Primary cortex neurons grown for 10 days under normal conditions were exposed to acute hyperoxia (60 min, 5 ATA $O_2$). This caused a significant increase in superoxide anion production. Ketone treatment decreased baseline superoxide production in a way that resembled the effect of the neuroprotective drug DTG. Both ketones and DTG prevented the hyperoxia-induced increase in superoxide production (n=110 cells analyzed/condition, * indicates p≤0.005).

Figure 5:
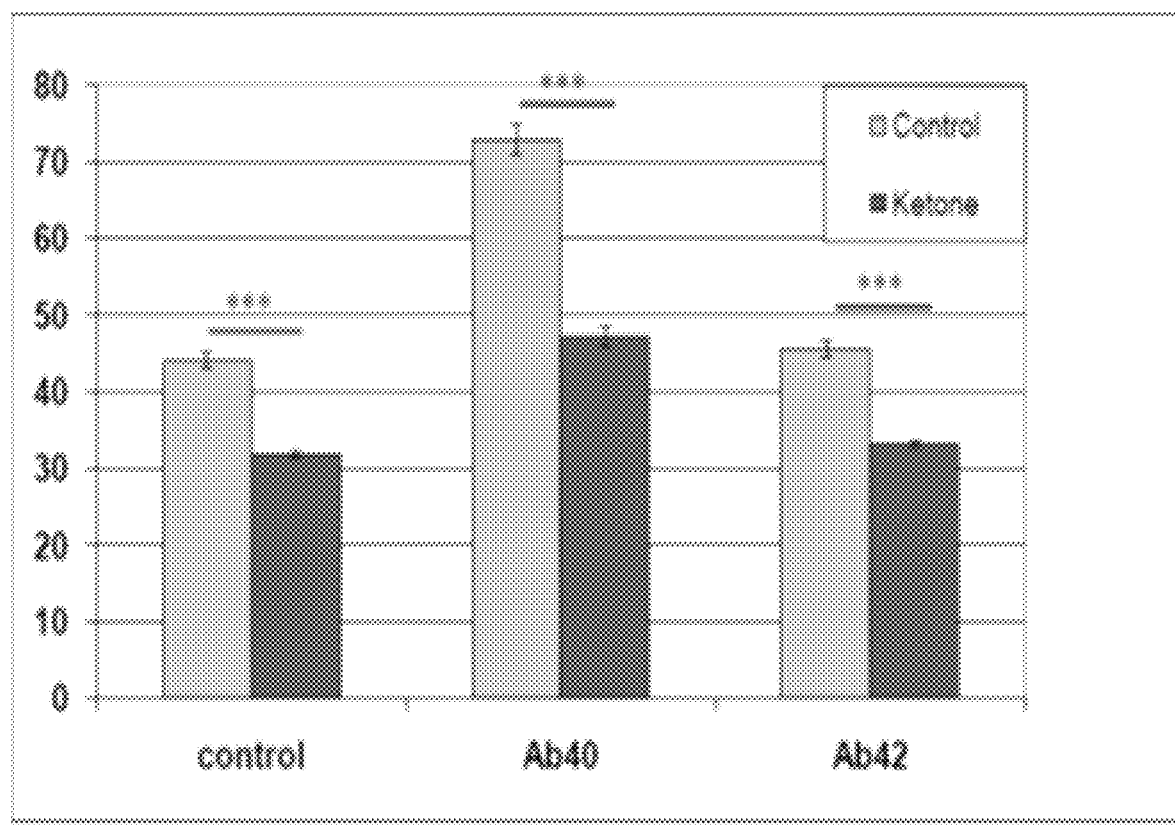
FIG. 5 is an image depicting the effect of ketones (2 mM ketones) on superoxide anion production in primary cortex neurons exposed to 1 mM of amyloid beta peptides (Aβ40, Aβ42), the peptide associated with Alzheimer's disease pathology. Ketones prevented excess ROS production associated with toxic levels of Ab.

The effect of ketones on superoxide anion production in primary cortex neurons is shown in FIG. 5. Ketones reduced oxidative stress in primary cultured neurons exposed to the proteins implicated in Alzheimer's disease. These results indicate that the administration of supplemental ketone esters can be used as a potential therapy against Alzheimer's disease.

EXAMPLE 2

Anticonvulsant Effect of Supplemental Ketones in Rats Exposed to Hyperbaric Oxygen (5 ATA $O_2$)

The details of this example are explained in the Materials and Methods section above. Briefly, the effects of ketone esters (KEs) in preventing CNS-OT in rats were assessed before, during and after $HBO_2$ exposure by measuring various parameters. Briefly, Sprague-Dawley rats (300-450 grams; 3 to 6 month old) were anesthetized (3-5% isoflurane) and implanted with a DSI (Data Sciences International) 4-ET radio-transmitters for recording diaphragmatic electromyogram (dEMG), electrocardiogram (ECG), electroencephalogram (EEG), core body temperature, and physical activity. Following from surgery (7 days), a single rat was placed in a separate plexiglass chamber inside a hyperbaric chamber (Reimers System, Inc—7.8 ATA MWP). The rat chamber was ventilated with pure $O_2$ while the hyperbaric chamber, containing the radio-receiver (DSI), was pressurized in parallel with air to 5 atmospheres absolute (ATA). Lower panels show Sensing and Telemetry modules implanted in the animals. Hyperbaric radiotelemetry allows precise monitoring of physiological parameters to assess the efficacy of ketones esters for prevention of CNS-OT.

Each rat underwent two dives at 5 ATA $O_2$ in the hyperbaric chamber, consisting of control (water gavage) and treatment, including R,S-1,3-butanediol AcAc diester (BD-AcAc$_2$) and R,S-1,3-butanediol (BD) given in random order. Our preliminary data showed that BD-AcAc$_2$ was the most effective KE against CNS-OT. In each case animals were gavaged about 30 minutes prior to diving. Total ketones are significantly elevated (>5 mM) about 30 minutes after gavaging BD-AcAc$_2$. One week after the control dive, the same rats were dived following treatment. Subsequent exposure to $HBO_2$, blood ketones and blood glucose were assayed using a blood glucose/ketone monitor (NovaMax Plus), commercially available kits (Caymen Chemical) or assayed at the metabolomics core facility at Case Western Reserve.

TABLE 1

| CNS-OT Prevention Protocols | | |
|---|---|---|
| Acute Treatment (ketogenic precursor) | Control (water) | Dose/volume/freq. (gavage) |
| R,S-1,3-butanediol AcAc diester (BD-AcAc$_2$) | 1-3 ml | 5-10 g/kg/3 ml/one dose |
| R,S-1,3-butanediol (BD) | 1-3 ml | 5-10 g/kg/3 ml/one dose |

Figure 6:
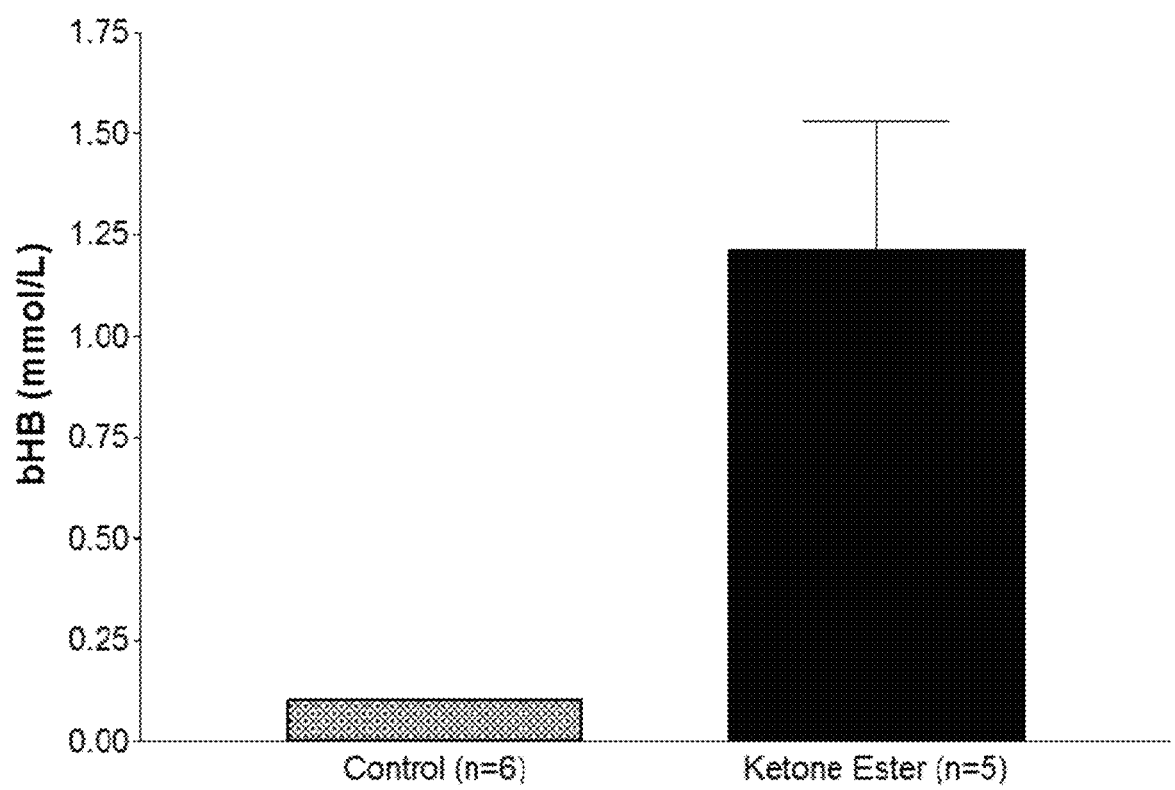
FIG. 6 is an image depicting the blood levels of ketones following oral administration of ketone ester. Specifically, the mean blood β-hydroxybutyrate (βHB) level is shown 2-3 hours after oral administration of R,S-1,3 butanediol acetoacetate monoester (BD-AcAc).

Blood levels of β-hydroxybutyrate (a ketone) following oral administration of ketone ester are illustrated in FIG. 6. As shown in the figure, within 30 minutes levels of blood ketones rose above 1 mM. The neuroprotective effect of ketones was proportional to the level of ketogenesis. The test measured only βHB, but it is estimated that total ketones (including acetoacetate) were approximately twice as high (~2.5 mM). Safe levels of ketosis are typically under about 8 mM.

Figure 7A:
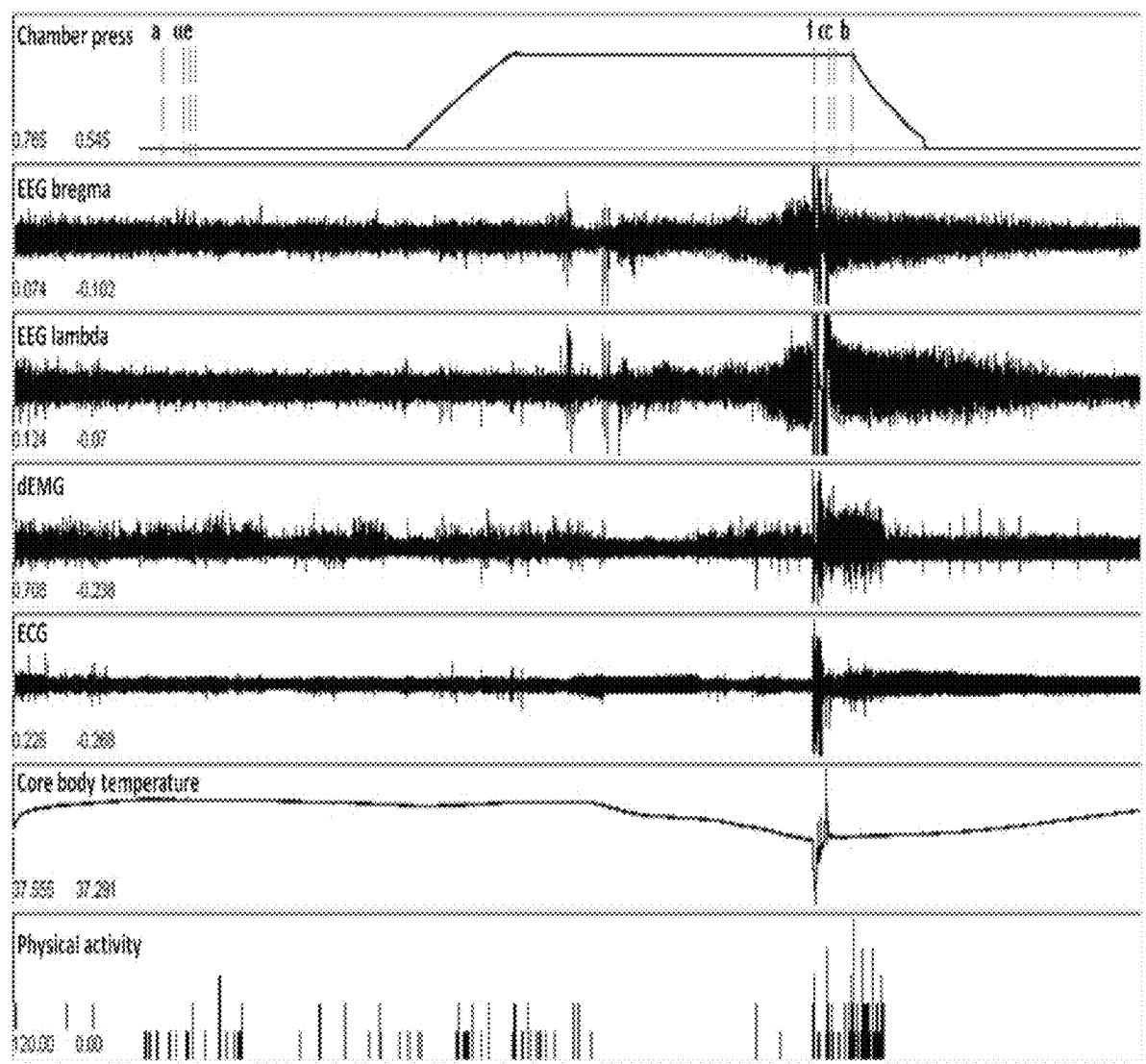
FIG. 7 is an image depicting an electroencephalogram (EEG) signal, showing the latency time to seizure during hyperbaric hyperoxia (HBO$_2$) at 60 pounds per square inch (PSI) (5 ATA O$_2$). EEG recordings are a measurement of brain seizure activity. (a) Seizure occurred in 8 minutes without ketone ester administered; (b) Seizure was delayed for 110 minutes following administration of KE (BD-AcAc).
Figure 7B:
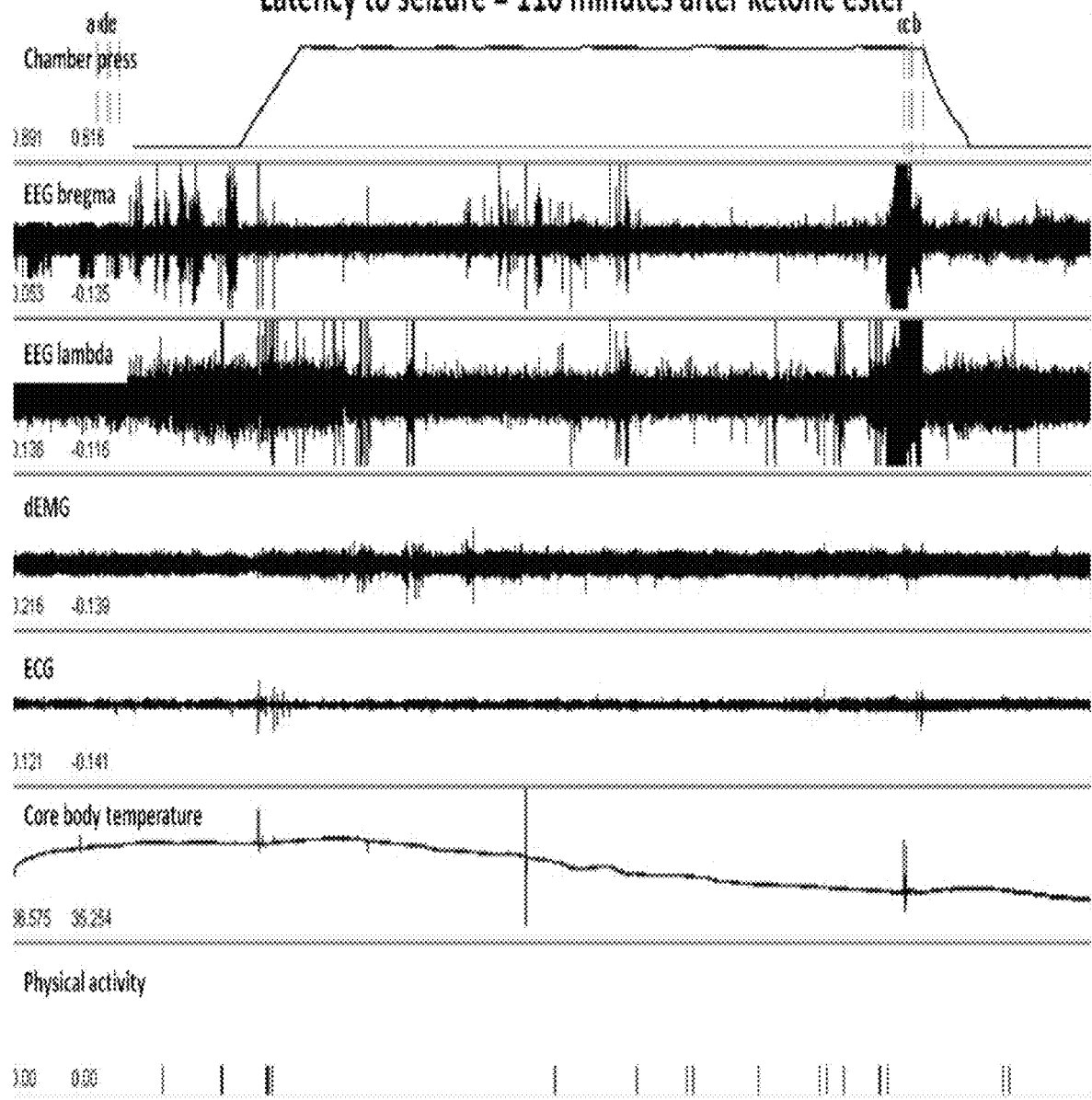

Data acquisition during $HBO_2$ at 60 PSI (5 ATA) is shown in FIG. 7. FIG. 7a illustrates raw data of a rat exposed to $HBO_2$ with a latency to seizure time of equal to about 8 minutes. When the same rat was given ketone ester, the animal resisted seizures from $HBO_2$ for about 110 min (FIG. 7b).

Figure 8:
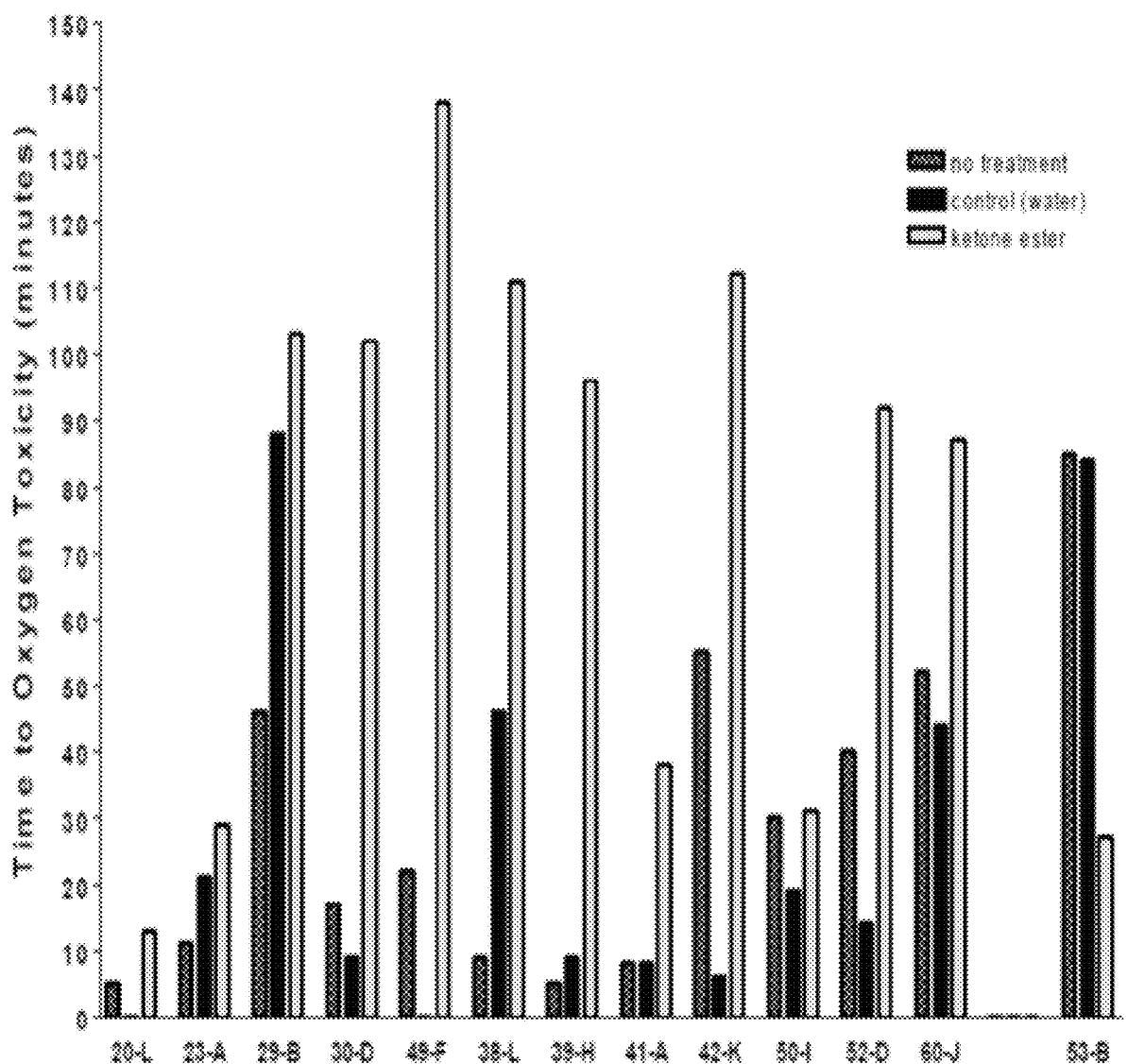
FIG. 8 is an image depicting the resistance to CNS oxygen toxicity (5 ATA O$_2$). The responses of individual rats with no treatment, control (water) and administration of ketone ester (R,S-1,3 butanediol acetoacetate monoester) are shown. As shown in the graph, intragastric administration of KE (BD-AcAc) protects rats against CNS oxygen toxicity. Administration of ketone ester (3 ml gavage) 30 minutes prior to hyperbaric oxygen (5 ATA O$_2$) exposure significantly increased latency time to first electrical discharge (FED) of EEG.
Figure 9:
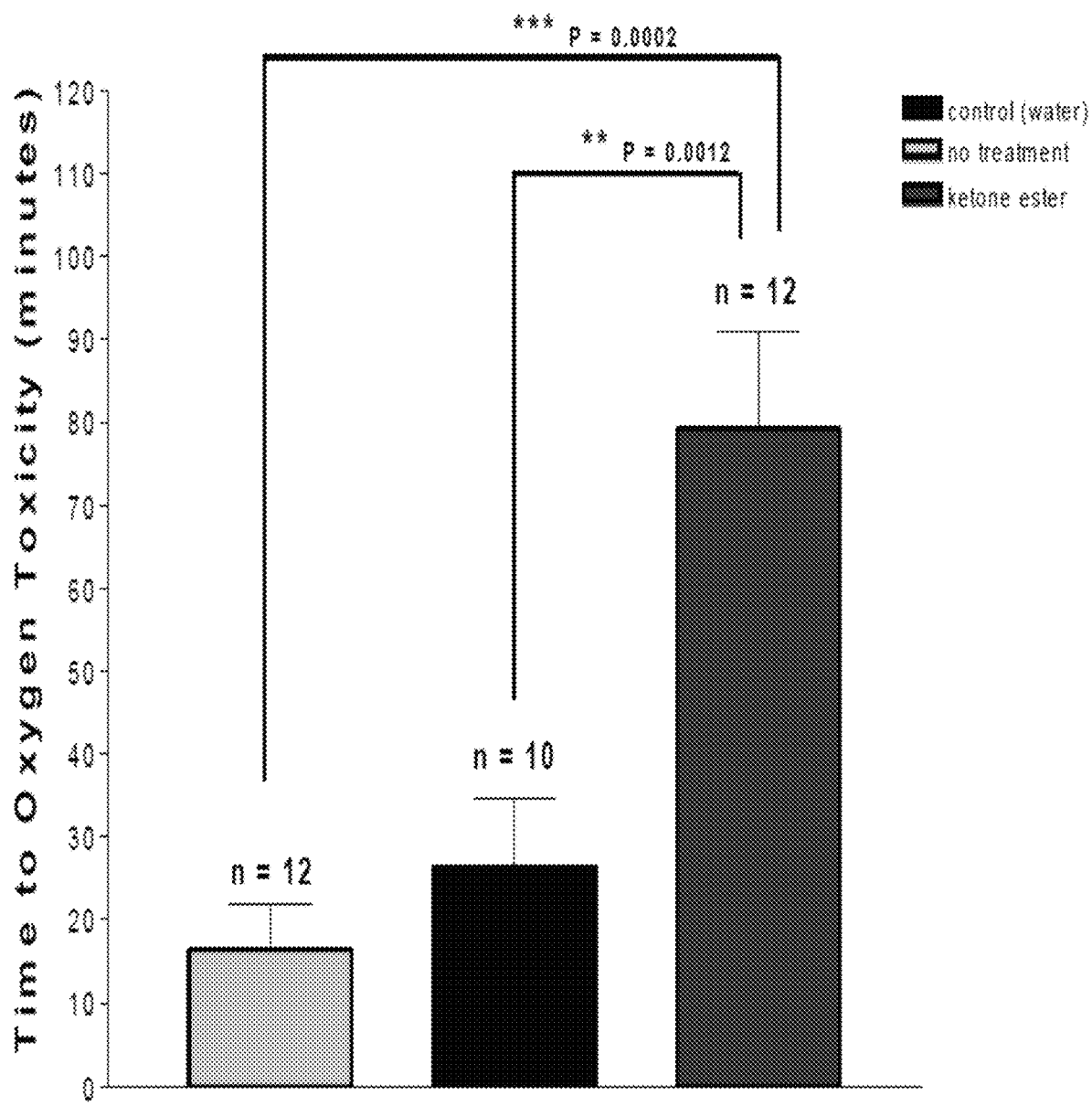
FIG. 9 is an image depicting the time to oxygen toxicity. The responses of rats without treatment, control (water) and administration of KE (BD-AcAc) are compared.

Responses from individual rats with no treatment, control (water) and ketone ester treatment are illustrated in FIG. 8. Administration of ketone ester (~3 mL) about 30 minutes prior to exposure to $HBO_2$ (5 ATA $O_2$) significantly increased the latency time to seizure (FIG. 9). Average time to seizure due to $HBO_2$ was measured as the time to the first electrical discharge in the EEG. Intragastric administration of ketone esters, specifically BD-AcAc$_2$, protected rats against CNS-OT. It was also found that administration of ketone esters (3 mL gavage) about 30 minutes prior to $HBO_2$ (5 ATA $O_2$) exposure significantly increased the latency time to first electrical discharge of EEG.

Radio-telemetry physiology experiments have confirmed the efficacy of two KEs (R,S)-1,3-butanediol acetoacetate monoester (BD-AcAc) and diester (BD-AcAc$_2$) in the prevention of CNS-OT in unanesthetized conscious rats. Administration of BD-AcAc and BD-AcAc$_2$, but not (R)-1,3-butanediol ester (BHB ester) or BD 30 minutes prior to exposure to HBO$_2$ (5 ATA O$_2$) significantly increased the latency time to seizure. The standard gavage volume was about 3 ml (~10 g/kg) for all treatments. All substances were gavaged in about a 3 ml dose (~10 g/kg). Average time to seizure from exposure to HBO$_2$ was measured and confirmed with video-EEG in untreated, control (water) and treatment groups. Precursors to AcAc, but not BHB, delayed CNS-OT, occasionally causing onset of pulmonary toxicity (after prolonged HBO$_2$ exposure).

The foregoing results have demonstrated the anticonvulsant effect of boosting ketogenesis and have shown that intragastric administration of ketone esters protects rats against CNS oxygen toxicity (seizures). A dietary supplement of ketone esters can rapidly elevate blood ketones and significantly maintain elevated ketone levels for several hours, even higher than levels achieved with fasting, CR or KD, and without fear of metabolic acidosis associated with diabetic ketoacidosis (DKA). A comparison of ketogenesis from starvation, KD, ketone ester, diabetic ketoacidosis and alcoholic ketoacidosis is shown in FIG. 10.

Figure 11:
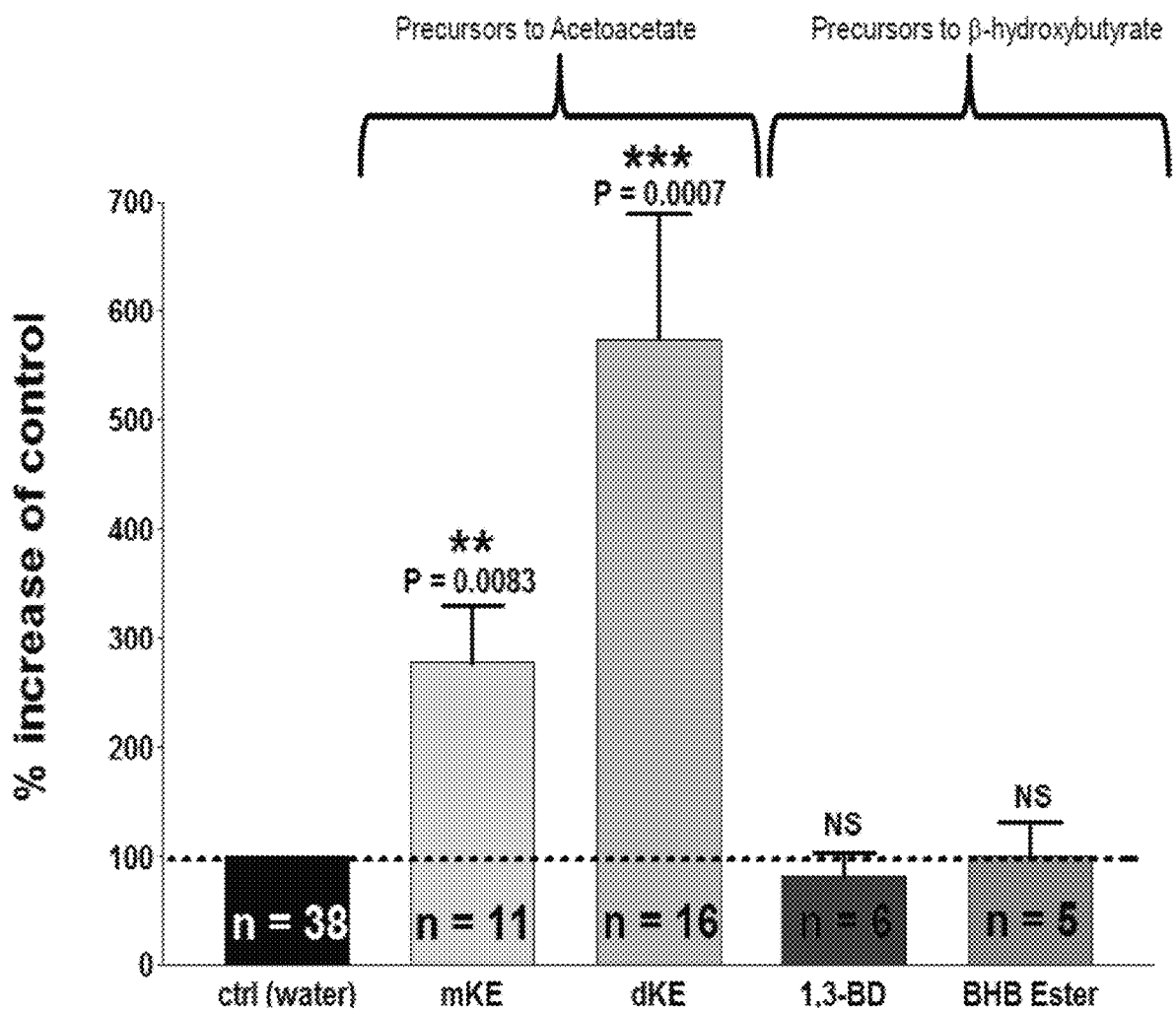
FIG. 11 is an image depicting the effect of ketone esters on latency to seizure in rats exposed to 5 ATA O$_2$. As shown in the graph, acute intragastric administration of ketone esters (10 g/kg), a non-ionized precursor to ketone bodies, given 30 min before diving, delayed seizures in rats exposed to 5 ATA O$_2$.

Acute intragastric administration of ketone esters (10 g/kg), a non-ionized precursor to ketone bodies, given 30 min before diving, delayed seizures in rats exposed to 5 ATA O$_2$ (FIG. 11). Acetoacetate monoester (mKE) and diester (dKE) increased the latency to seizure by 285% and 570%, respectively. 1,3-butanediol and β-hydroxybutyrate ester elevated blood levels of β-hydroxybutyrate, but had no effect on seizure latency. These results demonstrate the anticonvulsant effect of acetoacetate esters. Ketone esters, specifically BD-AcAc$_2$, increase latency to seizure in rats exposed to 5 ATA O$_2$. The data indicates increased resistance to oxygen-induced seizures (570Of the esters tested, the AcAc esters which are rich in BD-AcAc$_2$, provide the most effective neuroprotection against CNS-OT.

Figure 12:
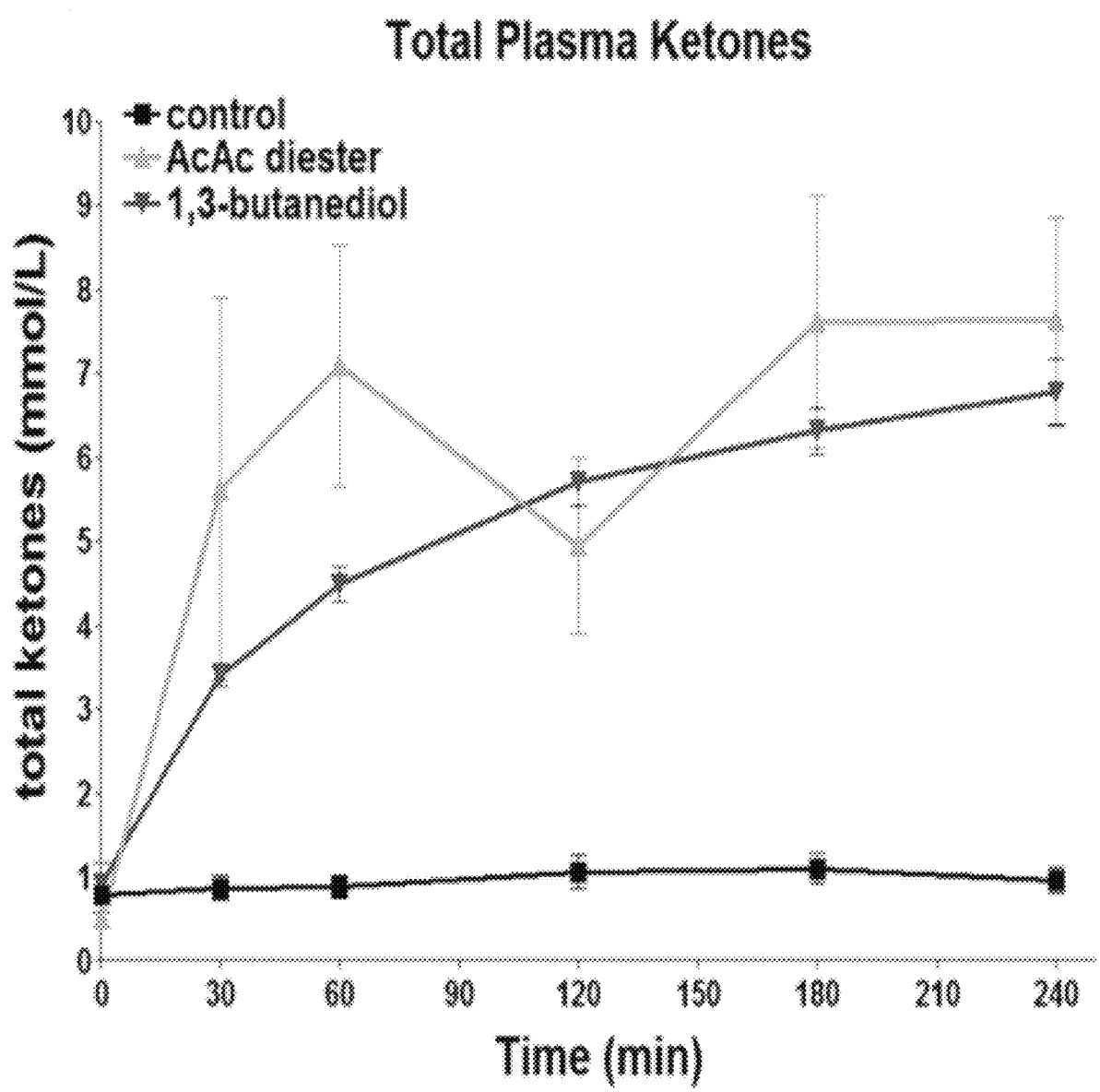
FIG. 12 is an image depicting ketone diester causes a rapid and sustained increase in total blood plasma ketones.

The ketone diester (dKE) was found to cause a rapid and sustained increase in total blood plasma ketones (FIG. 12). Blood plasma concentration of total ketones (BHB+AcAc) levels in adult Sprague Dawley rats (n=6 rats/group; 250 to 350 g) semi-fasted (18 hrs) and gavaged with 3 mL (~10 g/kg) of water (control), BD-AcAc$_2$) or BD are illustrated in FIG. 12. Ketone measurements were taken at 30, 60, 120, 180 and 240 minutes. Blood plasma was treated with sodium borodeuteride (NaB2H4) to stabilize ketone concentration and then assayed by GC-MS. The rapid rise relating to blood ketones from BD-AcAc$_2$ is due primarily from rapid desterfication in blood and tissues. Desterification of BD-AcAc$_2$ releases 1,3-butanediol, which is metabolized in the liver to BHB.

EXAMPLE 3

KE Induces Rapid and Sustained Elevation of BHB, AcAc and Acetone

Figure 13:
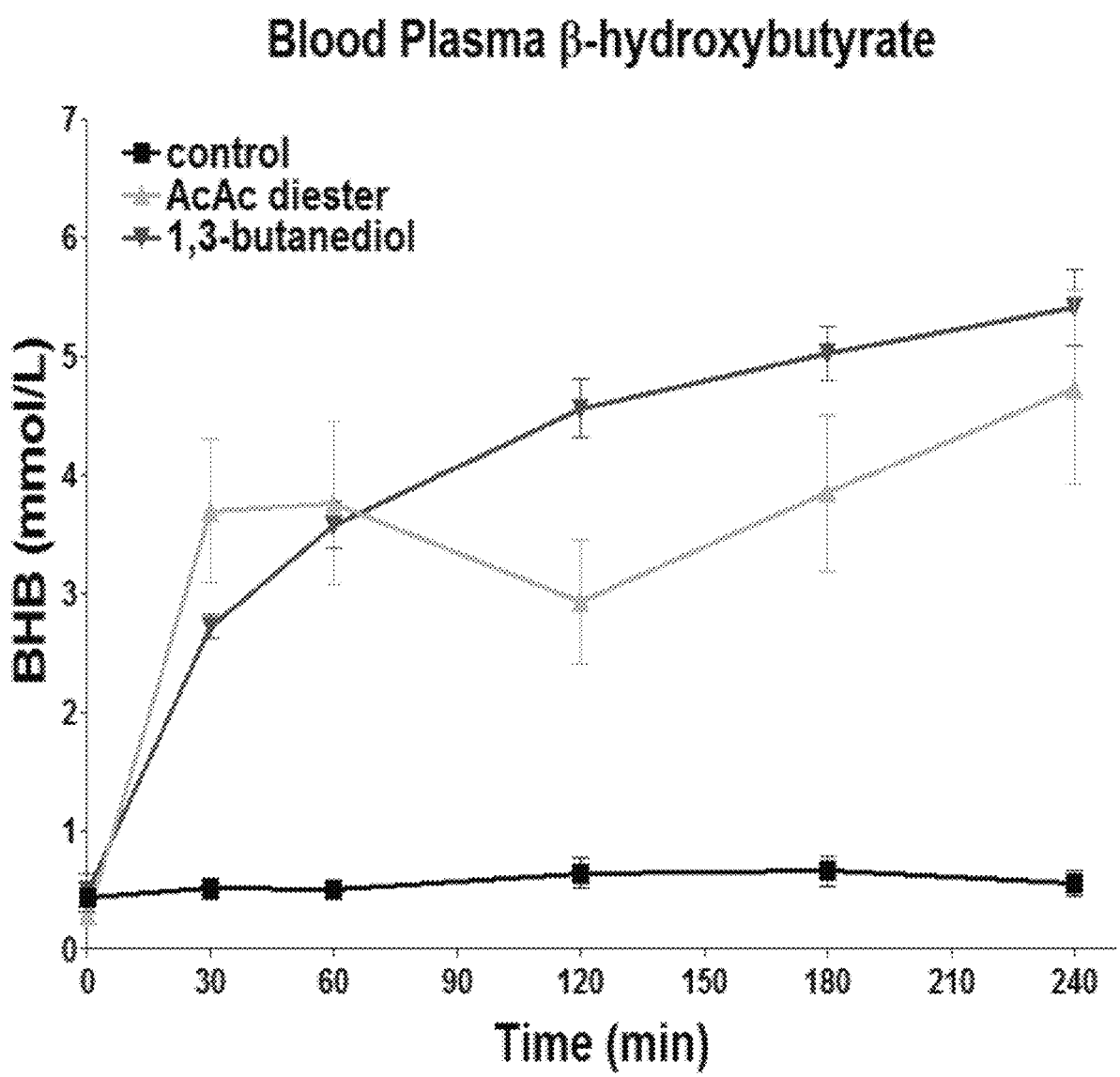
FIG. 13 is an image depicting blood plasma levels of BHB in rats (n=6 rats/group) semi-fasted (18 hrs) and gavaged with 3 mL (~10 g/kg) of water (control), R,S-1,3-Butanediol acetoacetate diester (BD-AcAc$_2$) (KE) or R,S-1,3-Butanediol (BD). As shown in the graph BHB level was elevated compared to control after administration of either ketogenic compound.

Blood ketones and glucose levels were examined following administration of water, KE and BD. FIG. 13 shows blood plasma levels of BHB in rats (n=6 rats/group) semi-fasted (18 hrs) and gavaged with 3 mL (~10 g/kg) of water (control), R,S-1,3-Butanediol acetoacetate diester (AcAc Diester) or R,S-1,3-Butanediol. Elevated BHB levels are demonstrated as compared to the control after administration of either ketogenic compound.

Figure 14:
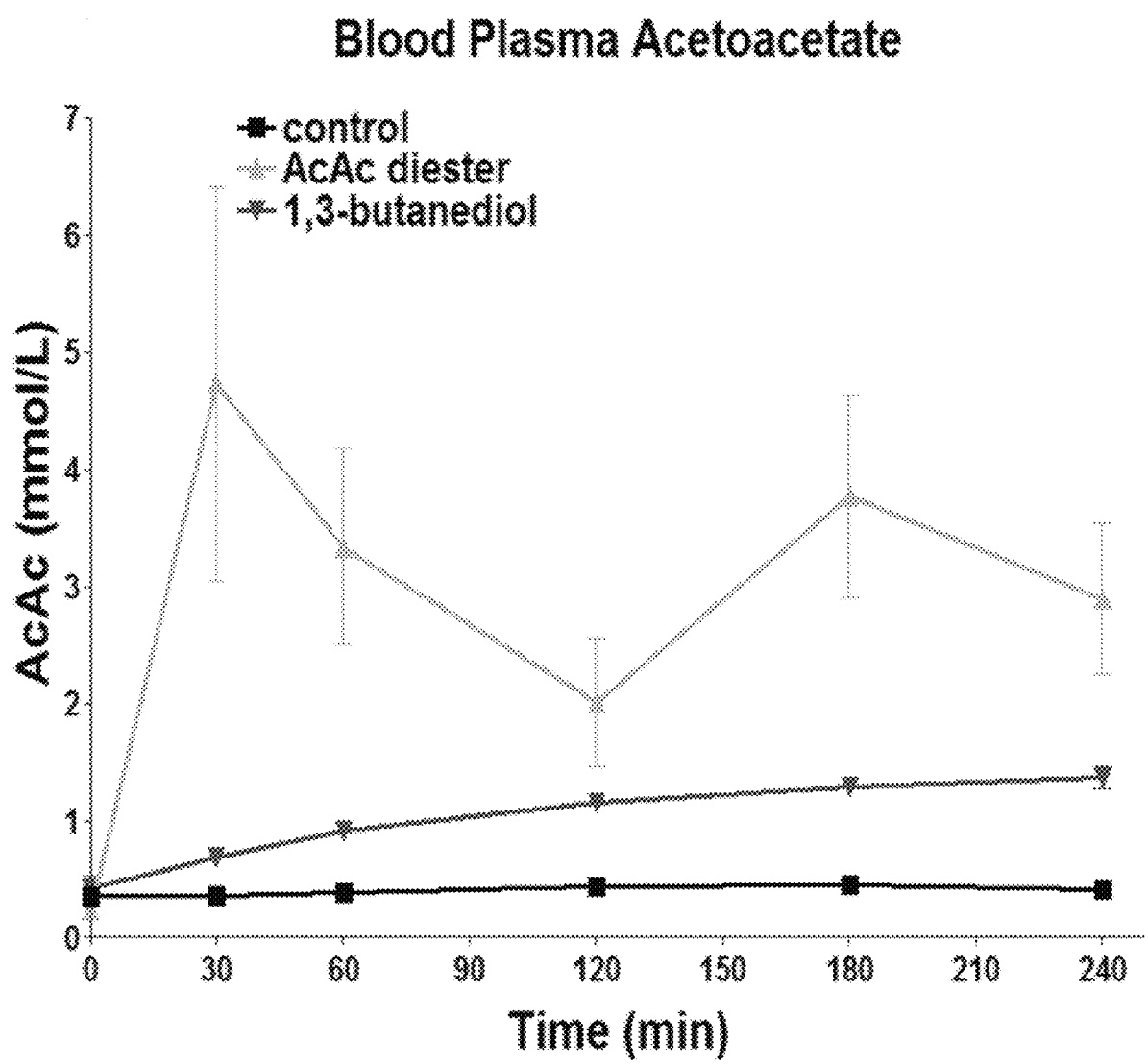
FIG. 14 is an image depicting blood plasma levels of AcAc in rats (n=6 rats/group) semi-fasted (18 hrs) and gavaged with 3 mL (~10 g/kg) of water (control), BD-AcAc$_2$ (KE) or R,S-1,3-Butanediol (BD). As shown in the graph, AcAc level was increased significantly by the ketone ester as compared to water or BD.

FIG. 14 shows blood plasma levels of AcAc in rats (n=6 rats/group) semi-fasted (18 hrs) and gavaged with 3 mL (~10 g/kg) of water (control), BD-AcAc$_2$ (AKE) or R,S-1,3-butanediol (BD). The results of FIG. 14 illustrate that AcAc level was increased significantly more by KE as compared to water or BD.

Figure 15:
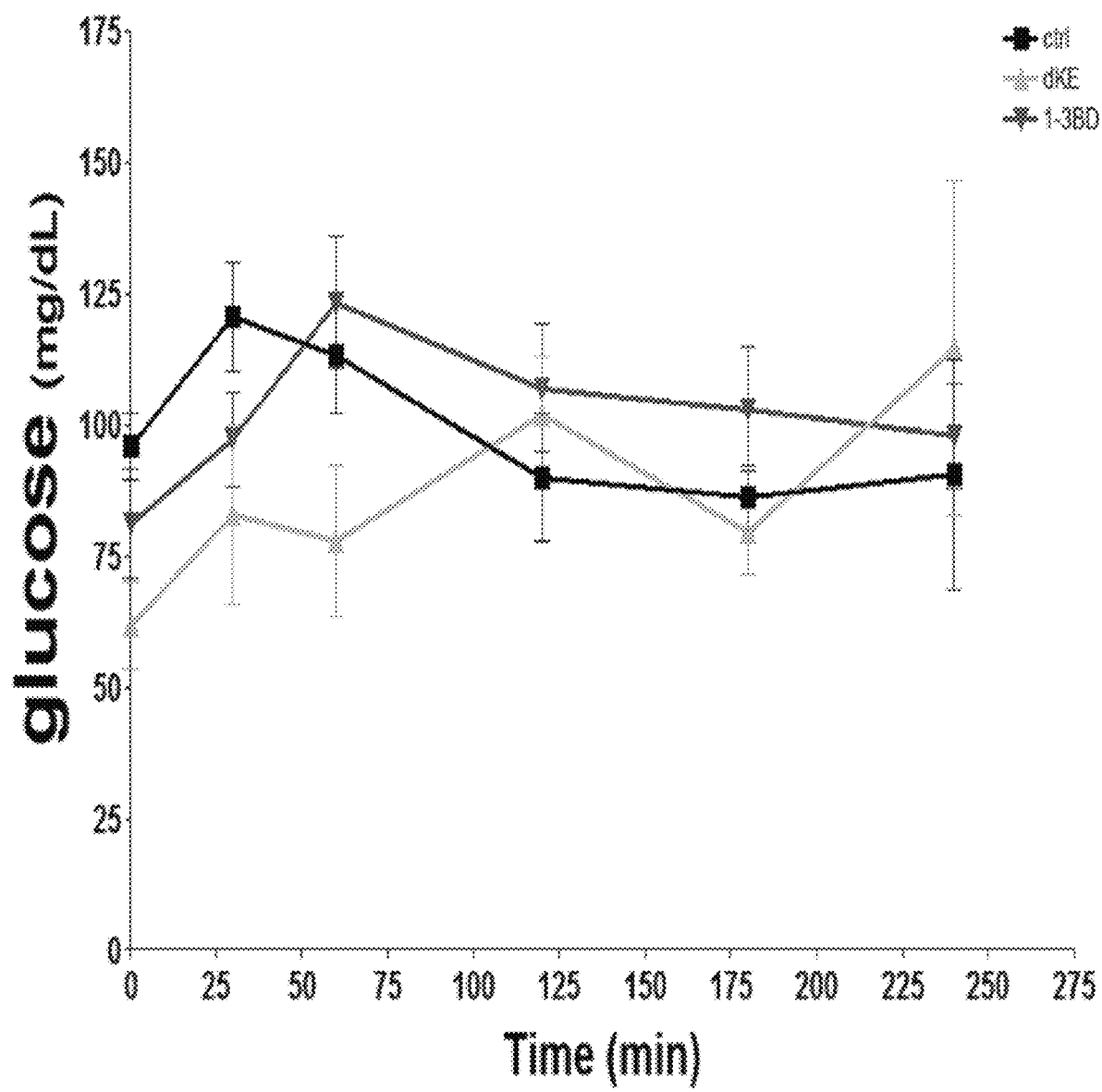
FIG. 15 is an image depicting the change in blood glucose in all groups in response to BD-AcAc$_2$, which represents a calorically dense (>6 kcal/gram) substance that does not elevate blood glucose. As shown in the graph, blood glucose did not change significantly in any group.

FIG. 15 illustrates that there is no change in blood glucose in all groups in response to BD-AcAc$_2$, which represents a calorically dense (6 kcal/gram) substance that does not elevate blood glucose. A sharp rise in blood glucose can induce a seizure and stimulate the progression of existing cancer. BD-AcAc$_2$ represents a novel therapeutic strategy to provide metabolic fuel without increasing blood glucose, which occurs following ingestion of carbohydrates and protein (via gluconeogenesis).

Figure 16:
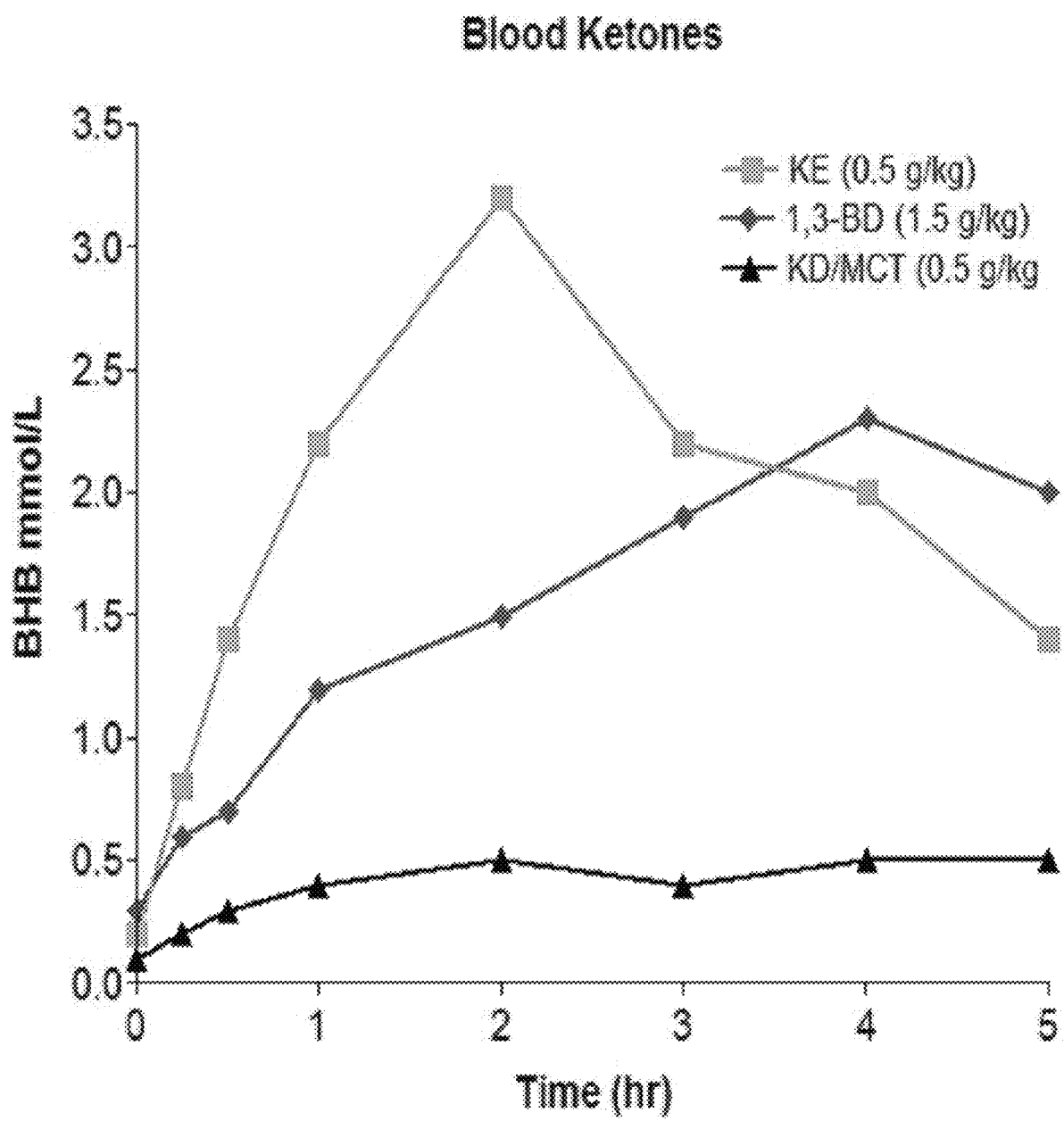
FIG. 16 is an image depicting a subject's blood levels of BHB in response to BD-AcAc$_2$ (KE), 1,3-butanediol (1,3-BD) and ketogenic diet (KD) supplemented with MCT oil.

Blood levels of BHB in response to BD-AcAc$_2$ (KE), 1,3-butanediol (BD) and ketogenic diet (KD) supplemented with MCT oil are shown in FIG. 16. Note the dose of KE relative to 1,3-BD. It takes considerably more 1,3-BD to raise BHB levels.

Figure 17A:
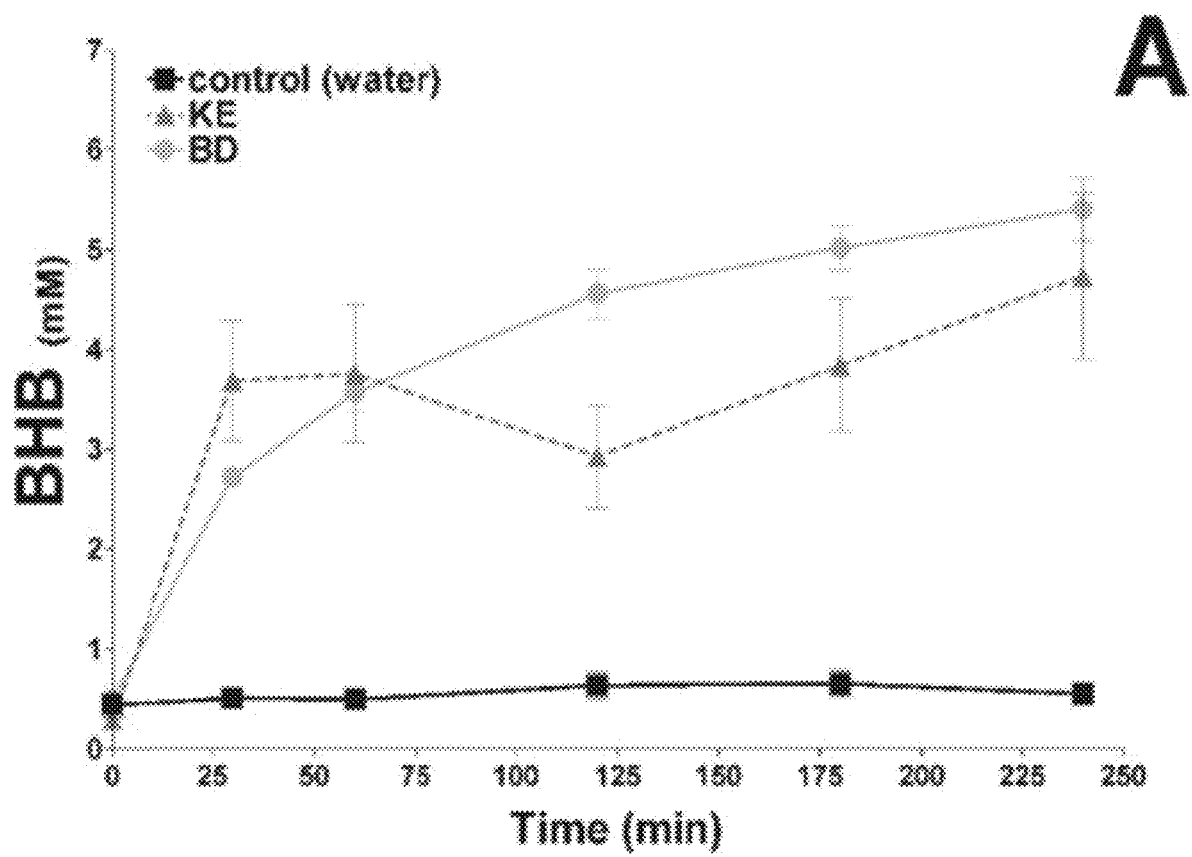
FIG. 17 is a series of images depicting blood ketones and glucose levels following administration of water, KE and BD. A (similar to FIG. 13): BHB level was elevated compared to control after administration of either ketogenic compounds; B (similar to FIG. 14): AcAc level was increased significantly more by KE compared to water or BD; C: acetone level increased significantly more after treatment with KE and D (similar to FIG. 15): blood glucose level did not change significantly in any group. n=6 rats/group; (NS=not significant).
Figure 17B:
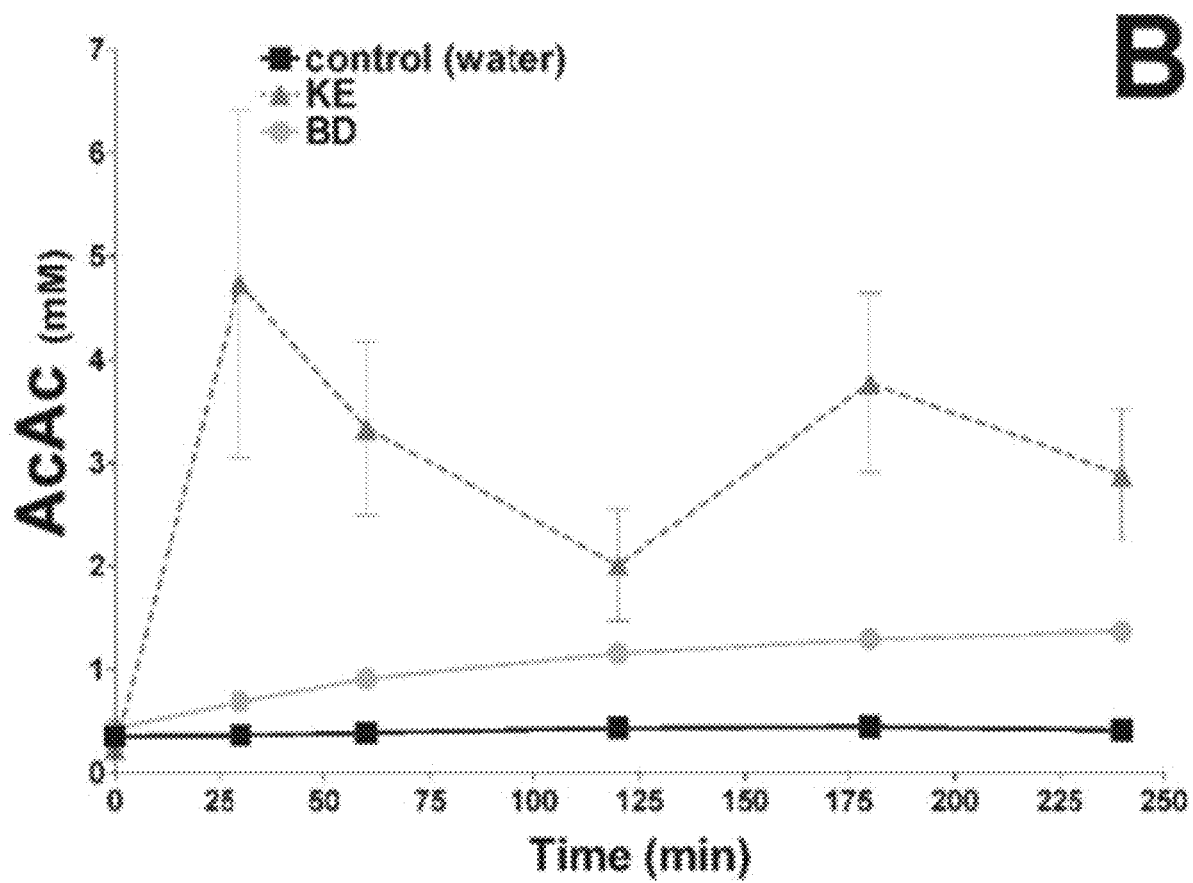
Figure 17C:
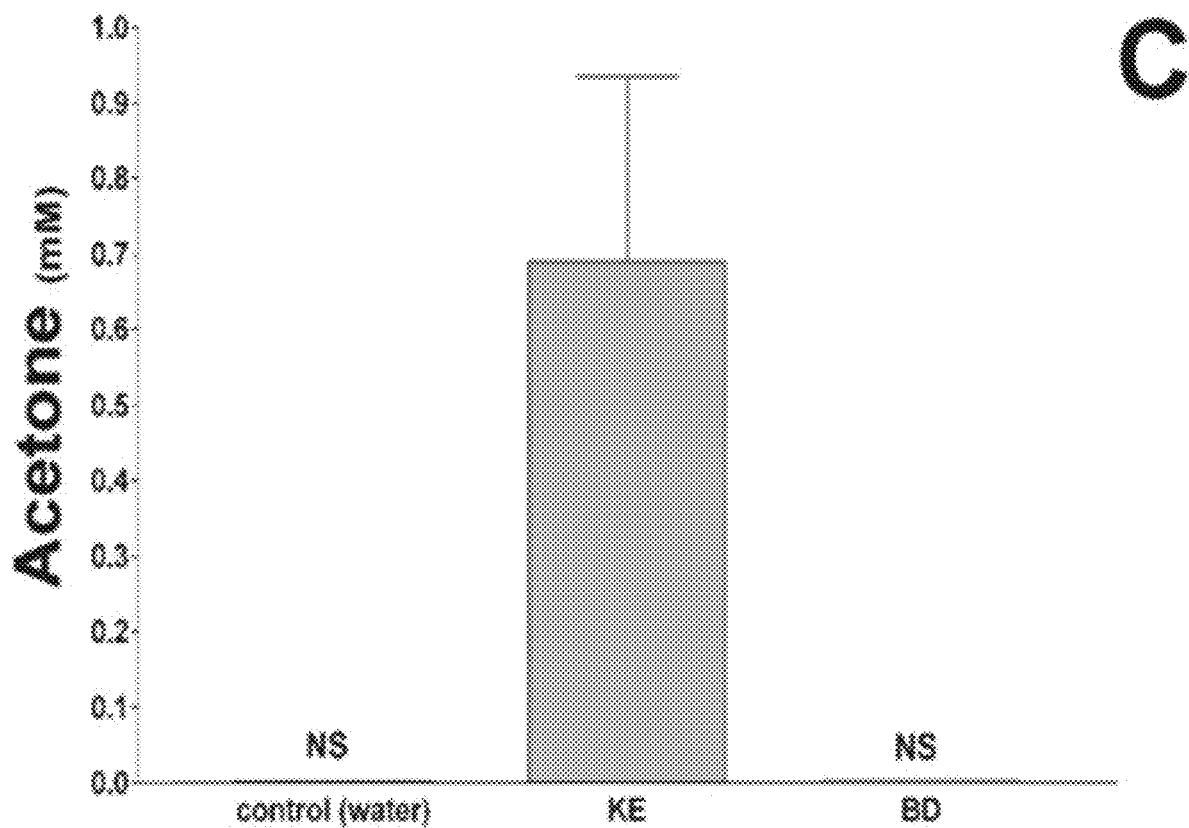
Figure 17D:
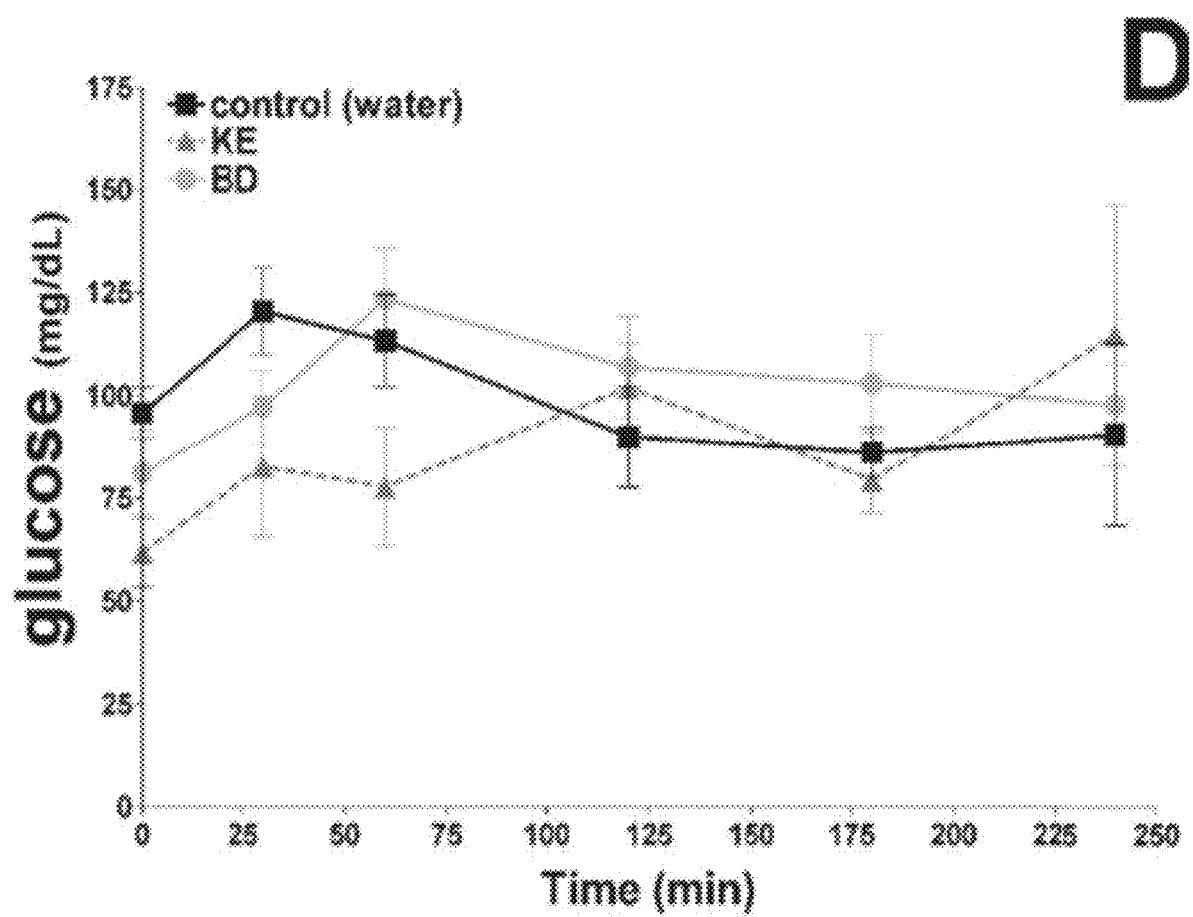

KE caused a significant increase in BHB and AcAc at 30 minutes, which remained elevated for 4 hours after intragastric administration (FIGS. 17A-C). BD administration caused similar elevation in BHB, but only modest elevation in AcAc relative to KE (FIG. 17B). The breakdown product of AcAc, acetone, was significantly higher at 60 minutes following KE, but not BD administration (FIG. 17C). In contrast, supplying calories (~6 kcal/gram) in the form of KE or BD had no significant effect on blood glucose levels relative to control (water) over 4 hrs (FIG. 17D).

EXAMPLE 4

KE-Induced Changes in Blood pO$_2$, pCO$_2$ and pH

Figure 18:
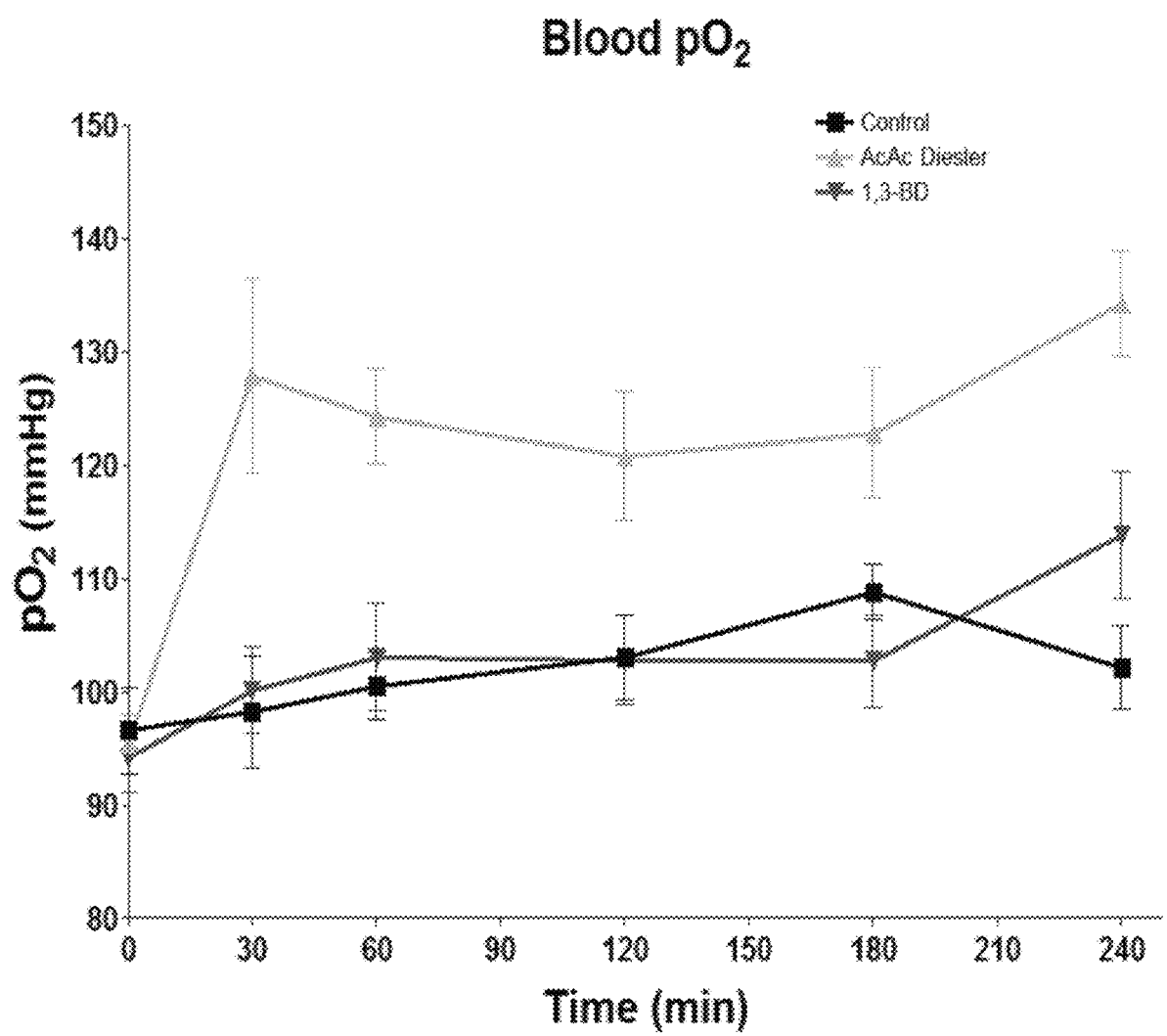
FIG. 18 is an image depicting to BD-AcAc$_2$ improves oxygenation in the blood as shown by pO$_2$ being elevated after administration of the ketone ester.
Figure 21A:
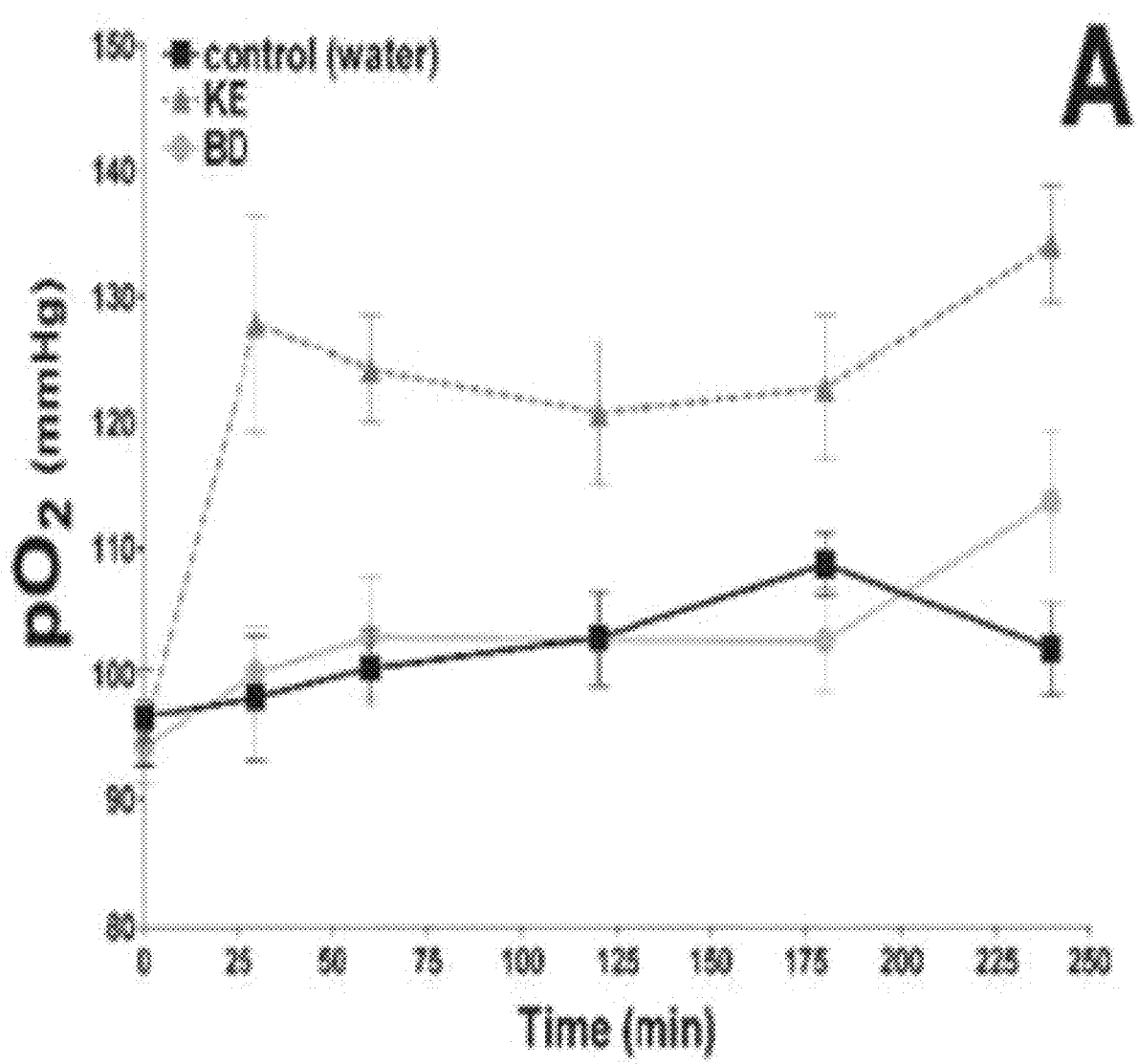
FIG. 21 is a series of images depicting blood gas values and pH following administration of water, KE and BD. A (similar to FIG. 18): pO$_2$ was elevated after administration of KE; B (similar to FIG. 19): pCO$_2$ was elevated after administration of BD; and C (similar to FIG. 20): pH was elevated compared to control after administration of either KE or BD; n=6 rats/group.

There were no differences in pO$_2$ after administration of water or BD, but pO$_2$ values were considerably higher in KE group and remained relatively hyperoxic (pO$_2$>120 mmHg) during the 4 hour experiment (FIGS. 15 and 21A). FIG. 18 shows BD-AcAc$_2$ (KE) improves oxygenation in the blood. BD-AcAc$_2$ may stimulate breathing by augmenting the neural control of autonomic regulation by stimulating acid-sensing neurons. Alternatively, the BD-AcAc$_2$ may reduce oxygen demands and maintain redox balance during hyperoxygenation by enhancing cellular respiration.

Figure 19:
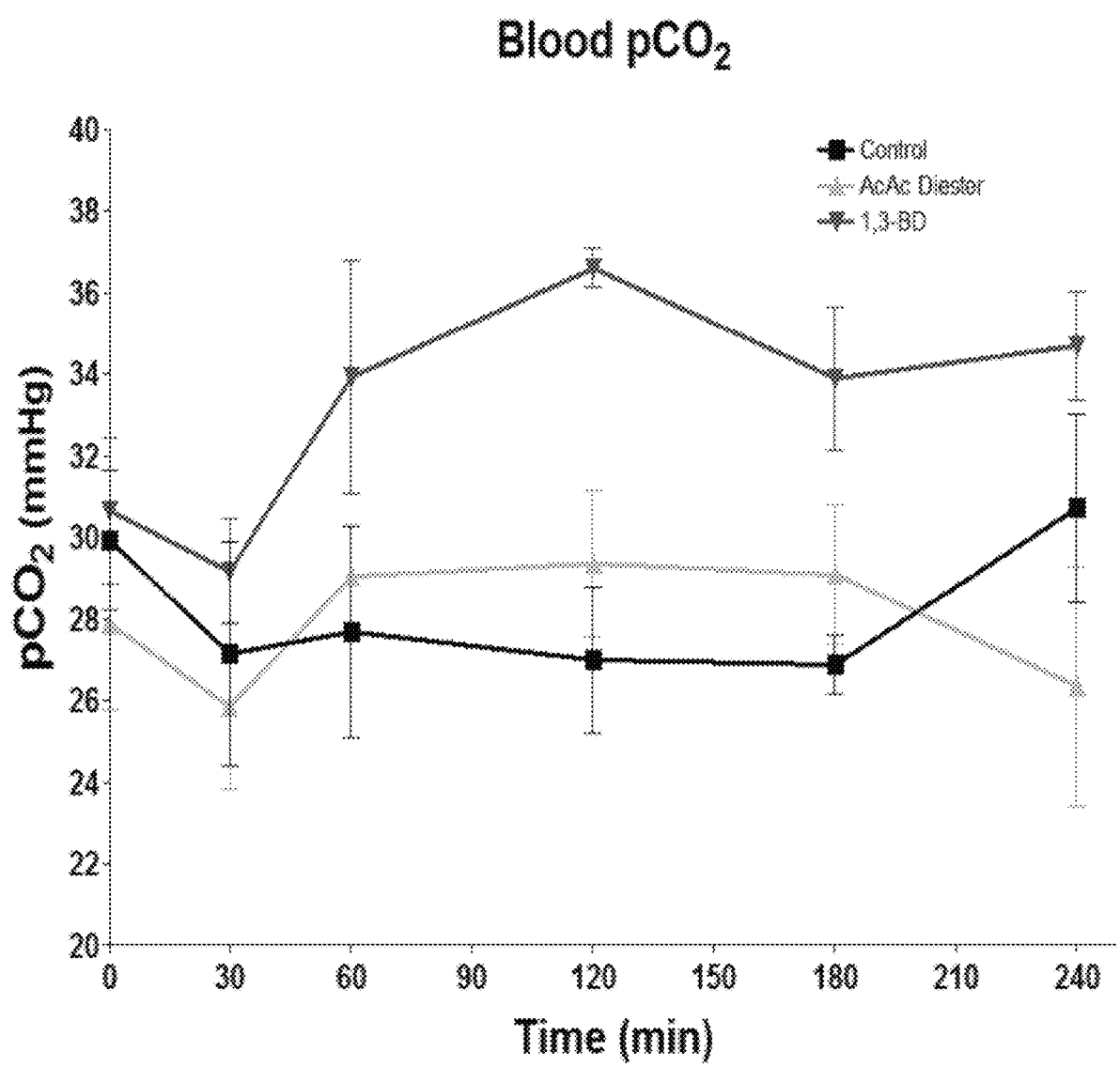
FIG. 19 is an image depicting pCO$_2$ is elevated after administration of BD which may indicate that suppression of CNS function due to intoxication from the di-alcohol is a potential problem with raising blood ketones with BD.
Figure 21B:
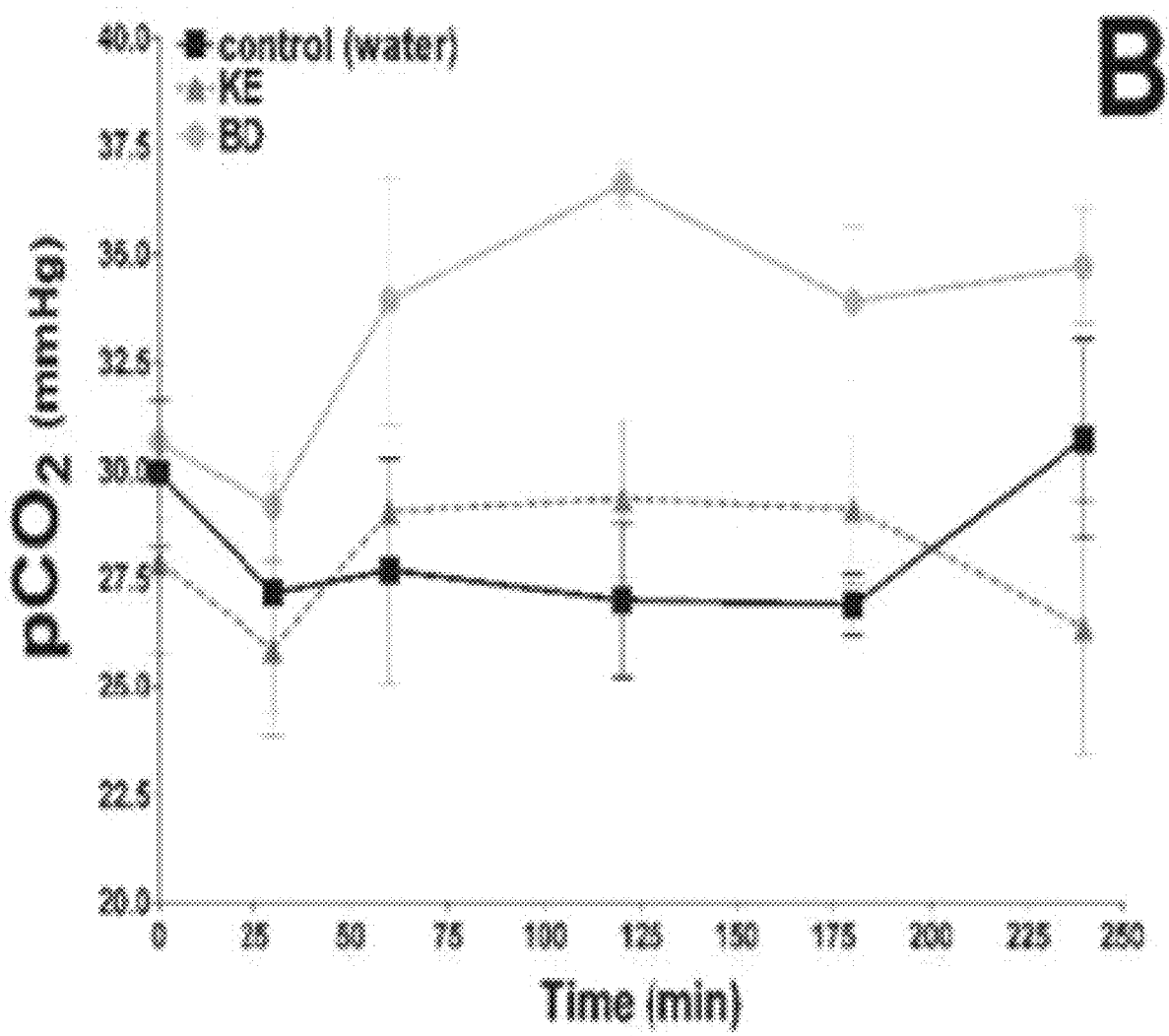

The pCO$_2$ of control and KE groups were normal, but was significantly higher with BD, although still normocapnic (FIGS. 19 and 21B). FIG. 19 shows that a potential problem with raising blood ketones with 1,3-butanediol is suppression of CNS function due to intoxication from the di-alcohol. The increased CO$_2$ with BD may be due to a depression in the neural control of respiration. BD-AcAc$_2$ raises blood ketones without causing an increase in blood pCO$_2$.

Figure 20:
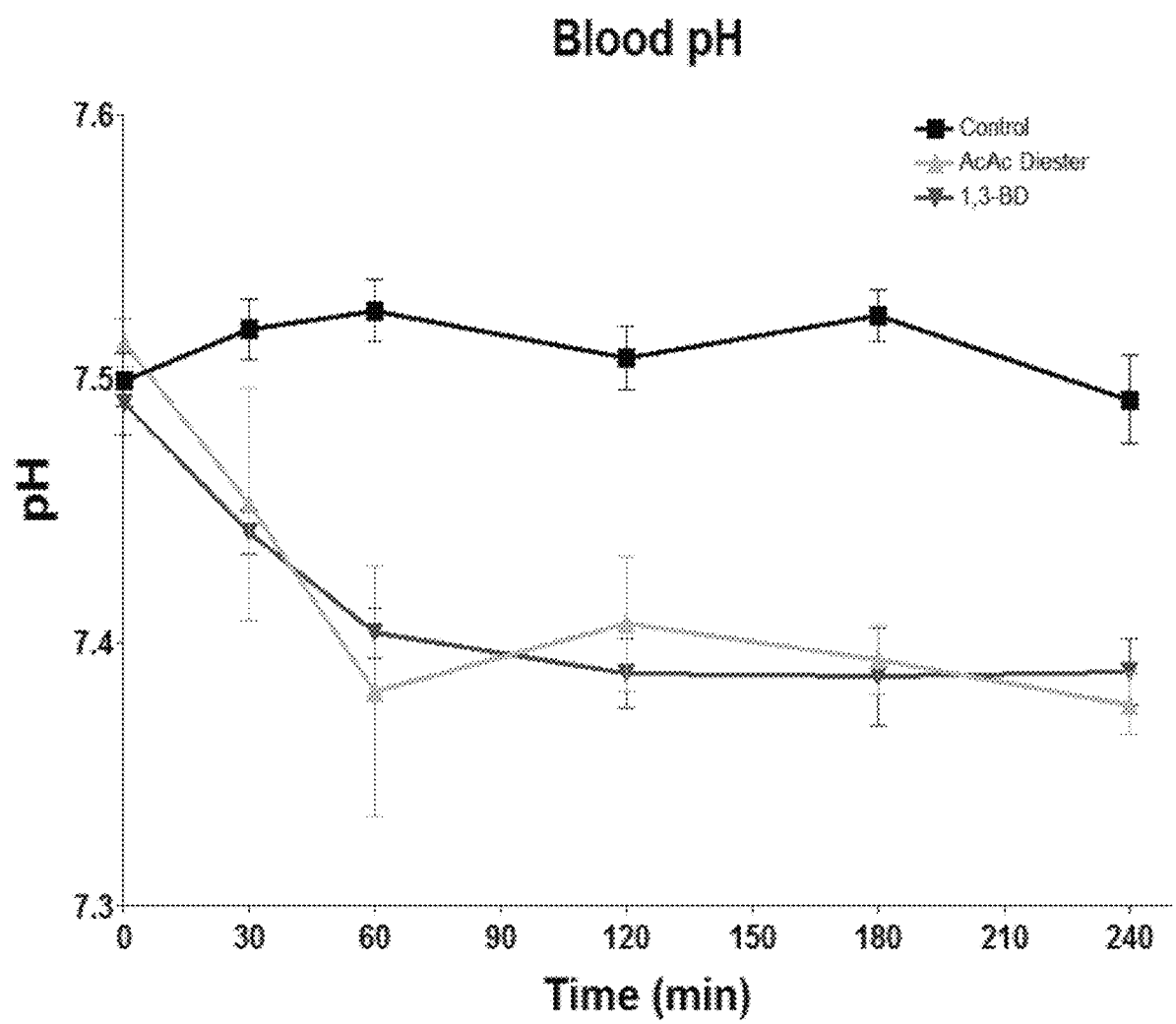
FIG. 20 is an image depicting increasing blood ketones with BD and BD-AcAc$_2$ causes a mild nonpathological acidosis (from 7.45 to 7.35).
Figure 21C:
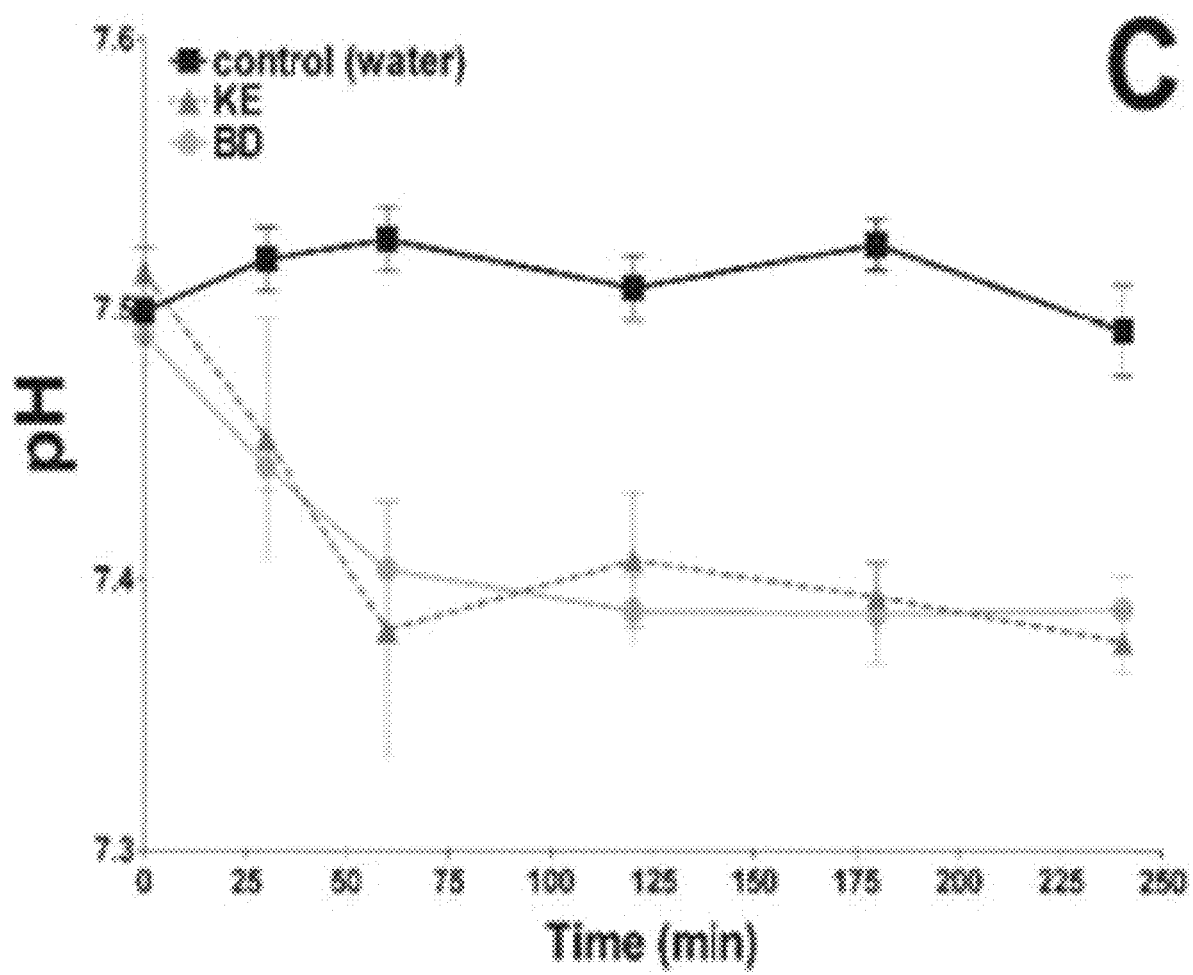

FIG. 20 shows increasing blood ketones with BD and BD-AcAc$_2$ causes a mild nonpathological acidosis. Mild acidosis is also common during the initial stages of the KD, and is typically attenuated with respiratory and renal compensation. Blood pH following KE or BD decreased compared to the control (pH~7.5), by a mean of 0.05 after about 30 minutes and 0.1 after about one hour. No significant difference in pH was found between KE and BD treatment (FIG. 21C).

EXAMPLE 5

KE Delays CNS-OT

Figure 22D:
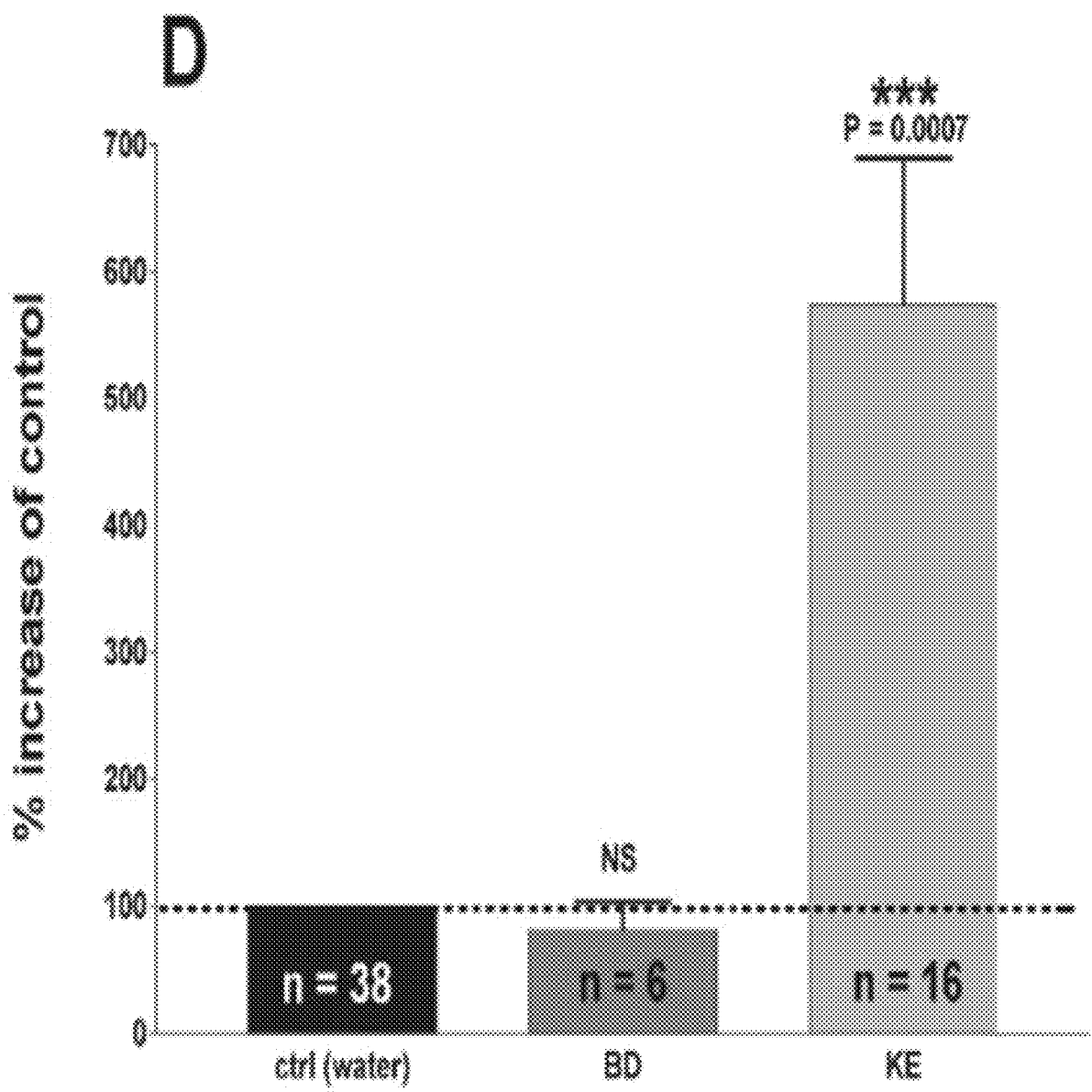
FIG. 22 is a series of images depicting examples of EEG raw data acquisition after the administration of (A) water (n=38), (B) BD (n=6) and (C) KE (n=16). (D) Percent change in LS relative to control: Oral administration of KE caused a significant increase in LS at 5 ATA O$_2$.

FIGS. 22 A, B and C show three examples of real time EEG recordings after intragastric administration of water, BD and KE, respectively. Latency to seizure (LS) was calculated as the percentage increase compared to the control (FIG. 22D). Following the intragastric administration of KE in 16 rats, the LS was significantly longer (574±115%, P<0.01). In contrast, BD administration did not delay CNS-OT.

As shown above, the inventors tested the potential of KE-induced therapeutic ketosis as a mitigation strategy against CNS-OT seizures. A single oral administration of the KE, BD-AcAc$_2$, caused: (1) rapid and significant elevations of BHB (>3 mM) and AcAc (>3 mM) that resulted in a sustained elevation of total ketones>6 mM for over 4 hrs; (2) significant elevation in acetone (~0.7 mM) within about 60 minutes; and (3) increased latency to seizure (LS)>570% compared to control (water) or BD, even though BD caused a significant increase in BHB.

EXAMPLE 6

KE Increase Blood Levels of Metabolic Intermediates and Redox-Dependent Signaling Pathways Associated with Anticonvulsant Neuroprotection As reported previously, the anticonvulsant mechanism of therapeutic ketosis is largely unknown (Bough and Rho 2007). The metabolic shift in substrate utilization (from glucose to ketones) stabilizes synaptic function (Hartman et al. 2007), and activates signaling pathways associated with synaptic stability. Preliminary evidence suggests that an elevation of specific ketones (AcAc) may be responsible for stabilization of synapses.

The buffering systems that maintain redox homeostasis are highly compartmentalized with three major redox couples: GSH/GSSG, oxidized/reduced thioredoxin and cysteine/cystine. These redox couples control the equilibrium between oxidized and reduced states of cysteines and methionines. Importantly, the redox couples are not in equilibrium with each other and therefore can be considered as independent nodes of redox control (Jones, 2004). The oxidation state, affecting proteins with thiol/disulfide switches, can be altered by metabolic changes, environmental stressors and disease states. Although the intracellular GSH/GSSG redox state appears to most accurately reflect the tissue antioxidant defense capability, the extracellular Cys/CySS redox state is known to regulate cell functions (Hansen, 2006). Evidence suggests that therapeutic ketosis will influence extracellular redox state (Milder and Patel 2011; Veech 2004).

Preliminary evidence suggests preferential utilization of specific ketones for brain function confers neuroprotection against CNS-OT. Chavko et al (1999) demonstrated fasting (24 hrs) delays CNS-OT, but this effect was independent of blood glucose or elevation of BHB (via 1,3-butanediol injection). The results here are consistent with Chavko et al. and support the lack of efficacy with BHB precursors (1,3-BD and 1,3-BD BHB ester). 1,3-BD AcAc monoester and 1,3-BD AcAc diester delays CNS-OT, but the mechanism is unknown, so it becomes essential to determine how ketogenesis affects markers of metabolic function and synaptic stability.

The anticonvulsant effects of KE can be enhanced with chronic administration, due higher levels of ketones (primarily AcAc and acetone), and metabolic adaption that involves upregulation of monocarboxylic acid transporters 1-4 (MCT 1-4) and activation of neuroprotective redox-sensitive metabolic signaling pathways.

Ketone bodies target a number of metabolic and neurophysiological signaling pathways (McNally and Hartman 2011), including reduced mitochondrial ROS production in response to an oxidative challenge (Kim do et al. 2010) and enhanced mitochondrial function (Veech et al. 2001). KE-induced neuroprotection is dependent on elevated ketones (AcAc, acetone), reduced oxidative stress and activation of neuroprotective pathways. Specific KE's confer protection against CNS-OT through multiple mechanisms involving enhanced brain metabolism and activation of neuroprotective redox-dependent signaling pathways. Neuroprotection against CNS-OT may require an elevation of ketone levels that mimics starvation (>3 mM), and that a significant rise in AcAc is essential.

EXAMPLE 7

Role of Supplemental Ketones in Preventing Hyperoxia-Induced Changes in Mitochondrial Function, Cellular Excitability, Oxidative Stress, Viability and Intracellular Ca$^{2+}$ in Primary Neuronal Cultures Mitochondrial dysfunction and ROS production underlie hyperoxia-induced cell damage (D'Agostino et al. 2007; Li et al. 2004b). Ketones prevent mitochondrial dysfunction and cell death in models of hypoxia (Masuda et al. 2005), Alzheimer's disease (Veech 2004), Parkinson's disease (Imamura et al. 2006; Kashiwaya et al. 2000) and amyotrophic lateral sclerosis (ALS) (Zhao et al. 2006). The neuroprotective effect of ketones is due to enhanced mitochondrial transmembrane potential ($\Delta\Psi$m) (Masuda et al. 2005) (Veech et al. 2002) and a reduction of mitochondrial ROS (Kim do et al. 2007; Kim do et al. 2010).

The inventors believe that mitochondrial dysfunction is the fundamental process triggering CNS oxygen toxicity. The in vitro experiments on primary neuronal cultures elucidate the mitochondrial/cellular mechanisms of ketone-induced neuroprotection by assessing cell viability and cellular correlates of mitochondrial function and oxidative stress.

Ketones may prevent hyperoxia-induced changes in mitochondrial function, superoxide production, intracellular Ca$^{2+}$ and thus preserve the resting V$_m$ and viability in primary neuronal cultures. There is considerable data to suggest that ketones can enhance mitochondrial function and preserve the resting membrane potential during oxidative challenges (Kim do et al. 2010; Veech 2004; Veech et al. 2002). These ketone-induced changes may prevent hyperoxia-induced changes in ROS, MDA and viability.

EXAMPLE 8

Effect of Supplemental Ketones on Plasma Membrane Structure and Visco-Elasticity in Artificial Membranes and Living Neurons Exposed to Graded Levels of Oxygen The inventors have previously demonstrated that MLP increases with elevated O$_2$ concentrations, and that hyperoxia-induced membrane surface damage in CNS cells can be resolved with AFM (D'Agostino et al. 2009). The main findings of the cellular and molecular studies to date are that nanoscopic membrane damage is an ultrastructural correlate of MLP resulting from hyperoxia. These changes in plasma membrane structure and function contribute to excitotoxicity and synaptic dysfunction associated with CNS-OT.

Plasma membranes are a major target for ROS because of the high concentration of oxidizable polyunsaturated fatty acids (e.g. PUFAs). Membrane PUFAs (e.g. docosahexanoic acid) are unique fatty acids because they alter basic membrane properties, including fluidity, elastic compressibility, ion permeability and resident protein functions (Shaikh et al. 2003; Stillwell and Wassall 2003). Hyperoxia-induced ROS production oxidizes membrane PUFAs and disrupts the formation, composition and distribution of lipid microdomains (lipid rafts) on the membrane surface (Brzustowicz et al. 2002; Shaikh et al. 2002; Stillwell and Wassall 2003). Lipid rafts are essentially sphingolipid and cholesterol rich platforms for cellular signal transduction, including ion channels, various transporters, G-proteins and kinases (Ahmed et al. 1997; Edidin 2003), cytoskeletal organization and lipid trafficking (Munro 2003).

The AFM is a valuable tool for studying the biophysical features of living and fixed cells at subnanometer resolution. Hyperbaric AFM (HAFM) and the recently developed hyperbaric confocal microscopy (HCM) are powerful techniques for resolving nanoscopic changes in the plasma membrane that result from oxidative damage. The studies to date have not determined if the hyperoxia-induced MLP was reversible or caused functional changes. The inventors test metabolic strategies that preserve neuronal membrane structure and function during exposure to hyperoxia-induced oxidative stress using technology that were recently developed and tested for use at hyperbaric pressure (D'Agostino et al. 2012). Evidence suggests that ketones are neuroprotective by virtue of their ability to enhance mitochondrial respiration, decrease ROS and preserve membrane fluidity (e.g. viscoelasticity) and electrical/synaptic stability (McNally and Hartman 2011). Thus, ketones may antagonize the membrane oxidizing effects of $HBO_2$.

The Anti-Convulsant Effect of KE

The mechanism of KE-induced delay in CNS-OT remains unknown, but evidence suggests that multiple factors contribute to the anticonvulsant effect of KE. These include 1) induction of starvation-level ketosis (Bitterman et al. 1997); 2) redox modulation (Kim do et al. 2010; Maalouf et al. 2007); 3) enhanced metabolic efficiency (Veech 2004); and 4) direct anticonvulsant effect of AcAc or acetone (Gasior et al. 2007; Likhodii et al. 2008; Rho et al. 2002). Each of these is discussed below.

KE Administration Produces "Starvation Ketosis"

The anticonvulsant effect of fasting and KD is well documented in humans and animal models and correlates with a rise in blood ketones (Bough and Rho 2007; McNally and Hartman 2011). Dietary-induced hepatic ketogenesis is dependent upon maintaining a low insulin/glucagon ratio, which quickly reverses with carbohydrate consumption, as seen in animal models and humans. These limitations make KE an attractive option for mitigating CNS-OT, and may represent a sought-after strategy for epilepsy to circumvent issues with compliance associated with KD (Rho and Sankar 2008). The data suggests that the anticonvulsant benefits of fasting and the KD are conferred with KE, even in rats eating a standard (carbohydrate-containing) diet ad libitum. Blood ketones following KE administration were higher than those typically reported in rats fasted 24-36 hrs (Chavko et al. 1999) or rats eating a KD (Bielohuby et al. 2011; Bough et al. 2002). Total blood ketones (BHB, AcAc and acetone) after 1 hr. averaged >6 mM, which is generally only achieved with prolonged starvation (>7 days) in humans (Cahill 2006). Acetone levels measured after KE administration were significantly elevated relative to water and BD, but below the levels typically needed to prevent seizures (>2 mM) in rats when given exogenously (Nylen et al. 2006). KE-induced blood acetone level (0.7 mM) was similar to brain acetone levels in epilepsy patients that have achieved complete seizure control with the KD (Seymour et al. 1999).

KE-induced Redox Effect

One explanation for the mechanism by which KE delays CNS-OT is a shift in redox homeostasis, or a preservation of redox state during a hyperoxia-induced oxidative stress. This mechanism is plausible if one accepts the "free radical theory of CNS-OT", which posits that the body's antioxidant defenses are overwhelmed by increased production of ROS (Gerschman et al. 1954). In support of this theory is the observation that brain and blood levels of ROS and reactive nitrogen species (RNS) increase just prior to $HBO_2$-induced seizures (Clark and Thom 1997; Demchenko et al. 2003). Previous research by the inventors has shown that superoxide production and neuronal excitability in the CA1 hippocampus is tightly coupled to tissue $O_2$ concentration ranging from 20-95% (D'Agostino et al. 2007). Considering the cellular and physiological effects of CNS-OT and the redox modulating effects of ketones (Maalouf et al. 2007; Veech 2004), it is not surprising that supra-physiological therapeutic ketosis significantly delays CNS-OT.

It is well established that therapeutic ketosis through fasting, calorie restriction and the KD activate numerous endogenous antioxidant pathways (Maalouf et al. 2009). These observations may explain how therapeutic ketosis, induced by fasting, protects against $HBO_2$-induced lipid peroxidation (Habib et al. 1990). Recently it has been shown that diet-induced ketogenesis improves mitochondrial redox state via activation of transcription factor Nrf2 (Milder et al. 2010), which is considered a master regulator of endogenous antioxidant regulation systems. Exogenous ketones also have direct antioxidant effects and protect against models of neurodegenerative disease (Maalouf et al. 2007). For example, ketones may prevent synaptic dysfunction by preserving brain metabolism during metabolic stress or oxidative stress from excess ROS production (Kim do et al. 2010; Veech 2004). These data are consistent with previous in vitro experiments, which showed that ketones significantly decrease superoxide production in primary neuronal cultures exposed to hyperoxia (D'Agostino et al. 2011).

An unexpected finding was that KE caused a significant and sustained increase in blood $pO_2$ levels of approximately 30%. It's conceivable that these changes in $PO_2$ result from KE-induced redox alterations in the neural control of autonomic regulation, including cardiorespiratory function (Mulkey et al. 2003). Current studies are being done to determine the specific contribution of KE on brain $O_2$ consumption, ventilatory drive and cardiorespiratory modulation preceding CNS-OT.

KE-induced Metabolic Therapy

The inventors believe CNS-OT results from oxidative-stress induced metabolic dysfunction. In this view, KE-induced therapeutic ketosis can be considered metabolic therapy. Metabolic-based therapies have been proven effective for seizure disorders and various acute and chronic neurological disorders (Greene et al. 2003; Kossoff and Hartman 2012). It is well known that restricting brain glucose by administering insulin in the absence of ketones causes rapid seizures in animal models and humans, and increases vulnerability to seizures. This phenomenon is observed with CNS-OT, whereby insulin-induced hypoglycemia enhances vulnerability to $HBO_2$-induced seizures (Beckman et al. 1982). It is clear that hyperoxic stress increases neuronal excitability (D'Agostino et al. 2007) and thus produces greater metabolic demands and substrate utilization (Torbati et al. 1983). The data suggest that KE-induced neuroprotection is conferred through enhancement of brain metabolism or synaptic stability by elevation of specific ketones, namely AcAc and acetone. Supplying alternative metabolic substrates to the brain may stabilize synaptic activity by mechanisms reported previously by other investigators, including increased Krebs cycle intermediates, antioxidant effects, increased GABA/glutamate ratio and activation of $K_{ATP}$ channels (Bough and Rho 2007; McNally and Hartman 2011).

Direct Effect of Specific Ketones

In previous studies, Chavko et al (1999) demonstrated that an elevation of the primary ketone body BHB (via 1,3-butanediol injection) did not delay CNS-OT. This observation is consistent with the finding that inducing ketosis by administration of BHB does not prevent seizures in animal models (Bough and Rho 2007). It is well known that BD produces ketosis, but primarily through the generation of BHB, and thus produces only low levels of AcAc and acetone (Tate et al. 1971). However, elevation of AcAc and acetone prevents acutely provoked seizures (e.g. chemical, electrical, audiogenic) in animal models (Likhodii et al. 2008; Rho et al. 2002). Acetone is relatively nontoxic (LD50>5 g/kg; rat) and has an anticonvulsant effect at subnarcotic concentrations (Gasior et al. 2007). Endogenous acetone levels are typically very low unless prolonged starvation is achieved (Cahill 2006). Collectively, these studies demonstrate that AcAc and acetone, but not BHB, have intrinsic anticonvulsant properties in standardized animal models of seizures. The inventors developed and tested a KE that elevated all three ketone bodies, but with the highest potential to elevate and sustain blood levels of AcAc (Ciraolo et al. 1995; Desrochers et al. 1995), which by spontaneous decarboxylation, would elevate acetone.

The data show that preferential utilization of AcAc and acetone, elevated by KE, delays CNS-OT. Evidence exists for a direct effect of these ketone bodies on hyperpolarizing neuronal membrane potential and reducing synaptic release of excitatory neurotransmitters (Yellen 2008). This data support the idea that $K_{ATP}$ channels are activated in the presence of ketone bodies (BHB and AcAc), but the mechanism of this activation is largely unknown. Work by Juge et al (2010) demonstrates that AcAc inhibited glutamate release by competing with Cl⁻ at the site of allosteric regulation (Juge et al. 2010). Very little is known about the anticonvulsant mechanism of acetone. Like other solvents, acetone can alter plasma membrane fluidity, which may counteract hyperoxia-induced alterations in plasma membrane function and structure (D'Agostino et al. 2009).

Clinical Considerations

There has been much confusion about ketosis in the medical community, especially the metabolic function of ketones (VanItallie and Nufert 2003). Many of these concerns result from viewing ketones as "metabolic poison" and the association of therapeutic ketosis with diabetic ketoacidosis (DKA). The pathological state of DKA produces "runaway ketosis" and results in ketone concentrations of 20 mM or greater, but is quickly reversed with insulin administration. A major concern that frequently arises with regards to ketosis is related to the mild metabolic acidosis caused by the accumulation of ketone bodies in the bloodstream. Normal blood pH range is 7.35 to 7.45, and may transiently drop lower during the initial stages of ketosis (Withrow 1980). However, blood pH typically rebounds into normal range as long as ketones are maintained <10 mM (Withrow 1980). The KE data and others (Ciraolo et al. 1995; Desrochers et al. 1995; Puchowicz et al. 2000) have demonstrated that the mild $H^+$ load from acute administration of BD-$AcAc_2$ does not induce a pathological metabolic acidosis. It needs to be determined how the chronic administration of KE influences blood pH. As with the KD, one would expect compensatory metabolic adjustments to buffer the $H^+$ load associated with chronic KE-induced ketosis. Furthermore, one would expect chronic KE administration to upregulate ketone transports and further augment the anticonvulsant effects of KE.

The beneficial effects of fasting or KD-induced ketosis have been demonstrated in a variety of neurological disorders (Freeman and Kossoff 2010). KE represents an innovative strategy for prevention of CNS-OT and possibly epilepsy. KE may offer an alternative to the KD or a means to enhance the KD as a "food supplement". Similar to the KD, it is unlikely that the anticonvulsant effect of KEs can be unified into a single mechanism or a final common pathway. Evidence for KE working through novel mechanisms is supported by the fact that KE works when AEDs fail (Bitterman and Katz 1987; Tzuk-Shina et al. 1991). Thus, the KE may activate mechanisms other than those targeted by any specific AED, or even combinations of AEDs. Surprisingly, no commercially available AEDs attempt to mimic the effect of the KD by exploiting the anticonvulsant and neuroprotective effects of therapeutic ketosis with KEs. The development and testing of KEs represent a promising therapeutic mitigation strategy for CNS-OT and seizure disorders, since there is ongoing effort to develop a "Ketogenic diet in a Pill" (Rho and Sankar 2008).

In light of the foregoing, the inventors found that 1) oral administration of ketone ester is neuroprotective against seizures resulting from CNS oxygen toxicity in rats, 2) supplemental ketones reduce superoxide production in cultured cortex neurons exposed to hyperbaric oxygen and Aβ-42, and 3) ketones decrease proliferation and viability in U87 glioma. These observations support the therapeutic effect of ketones for seizure disorders, Alzheimer's disease and malignant brain cancer.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of increasing latency time and resistance to hyperoxia-induced seizure due to hyperbaric oxygen ($HBO_2$) exposure comprising inducing mild ketosis in a subject in need of hyperbaric oxygen by administering a therapeutically effective dose of a composition comprising R,S-1,3-butanediol acetoacetate and R,S-1,3- butanediol acetoacetate diester in a sufficient amount to elevate blood β-hydroxybutyrate (BHB) and acetoacetate (AcAc) ketones and $pO_2$ levels and maintain the elevated level for about four (4) hours wherein BHB and AcAc ketones are elevated in the blood to a total amount of at least 1 mM,
   wherein the composition is administered at least 30 minutes prior to hyperbaric oxygen exposure,
   wherein administration of the composition does not increase $pCO_2$ in blood, and reduces superoxide anion production and thus oxidative stress, and
   wherein the composition is administered with an unrestricted diet.

2. A method of protecting against hyperoxia-induced oxidative stress comprising inducing mild ketosis in a subject in need of hyperbaric oxygen by administering a therapeutically effective dose of a ketone ester derived from acetoacetate in a sufficient amount to elevate blood β-hydroxybutyrate (BHB) and acetoacetate (AcAc) ketones and $pO_2$ levels in blood and maintain the elevated levels for about four (4) hours wherein BHB and AcAc ketones are elevated in the blood to a total amount of at least 1 mM, wherein administration of the ketone ester derived from acetoacetate does not increase $pCO_2$ in blood, and reduces superoxide anion production and thus the hyperoxia-induced oxidative stress in the subject,
   wherein the ketone ester derived from acetoacetate is administered at least 30 minutes prior to hyperbaric oxygen exposure, and
   wherein the ketone ester is administered with an unrestricted diet.

3. The method of claim 2, wherein the ketone ester is a R,S-1,3-butanediol acetoacetate ester.

4. The method of claim 3, wherein the ketone ester is R,S-1,3-butanediol acetoacetate monoester.

5. The method of claim 3, wherein the ketone ester is R,S-1,3-butanediol acetoacetate diester.

6. The method of claim 3, wherein the ketone ester is a combination of R,S-1,3-butanediol acetoacetate monoester and R,S-1,3-butanediol acetoacetate diester.

7. A method of protecting against central nervous system oxygen toxicity in a subject in need of hyperbaric oxygen comprising:
   administering a therapeutically effective dose of a ketone ester derived from acetoacetate in a sufficient amount to elevate blood β-hydroxybutyrate (BHB) and acetoacetate (AcAc) ketones and $pO_2$ levels in blood and maintain the elevated levels for four (4) hours or more wherein BHB and AcAc ketones are elevated in the blood to a total amount of at least 1 mM, wherein administration of the ketone ester derived from acetoacetate does not increase pCO2 in blood, and reduces superoxide anion production and hyperoxia-induced oxidative stress in the subject,
   wherein the ketone ester derived from acetoacetate is administered at least 30 minutes prior to hyperbaric oxygen exposure, and
   wherein the ketone ester is administered with an unrestricted diet.

8. The method of claim 7, wherein the ketone ester is a R,S-1,3-butanediol acetoacetate ester.

9. The method of claim 8, wherein the ketone ester is selected from the group consisting ofR,S-1,3-butanediol acetoacetate monoester; R,S-1,3-butanediol acetoacetate diester; and combinations thereof.

10. The method of claim 1, wherein the blood ketone level is elevated to greater than 1 mM within 30 minutes.

11. The method of claim 1, wherein the blood $pO_2$ level is elevated to about 30% within 30 minutes.

* * * * *